(12) United States Patent
Jackson

(10) Patent No.: US 11,969,351 B2
(45) Date of Patent: Apr. 30, 2024

(54) SYSTEMS AND METHODS FOR MAGNETIC JOINTS

(71) Applicant: James M. Jackson, Huntington Beach, CA (US)

(72) Inventor: James M. Jackson, Huntington Beach, CA (US)

( * ) Notice: Subject to any disclaimer, the term of this patent is extended or adjusted under 35 U.S.C. 154(b) by 0 days.

(21) Appl. No.: 18/260,465

(22) PCT Filed: Feb. 2, 2023

(86) PCT No.: PCT/US2023/012208
§ 371 (c)(1),
(2) Date: Aug. 10, 2023

(87) PCT Pub. No.: WO2023/150221
PCT Pub. Date: Aug. 10, 2023

(65) Prior Publication Data
US 2023/0397996 A1    Dec. 14, 2023

Related U.S. Application Data

(60) Provisional application No. 63/306,208, filed on Feb. 3, 2022.

(51) Int. Cl.
*A61F 2/38* (2006.01)
*A61F 2/30* (2006.01)

(52) U.S. Cl.
CPC .......... *A61F 2/3836* (2013.01); *A61F 2/3859* (2013.01); *A61F 2/3868* (2013.01); *A61F 2002/30079* (2013.01)

(58) Field of Classification Search
CPC .. A61F 2/30; A61F 2/40; A61F 2/3859; A61F 2/389; A61F 2/3868
See application file for complete search history.

(56) References Cited

U.S. PATENT DOCUMENTS 4,024,588 A   5/1977  Janssen et al.
5,595,563 A   1/1997  Moisdon
(Continued)

FOREIGN PATENT DOCUMENTS

| CN | 201870774 U | 6/2011 |
| JP | 4284565 B2 | 6/2009 |
| WO | WO97/03661 A1 | 8/1997 |

OTHER PUBLICATIONS

PCT International Search Report and Written Opinion for PCT/US2023/012208, James M. Jackson, Forms PCT/ISA/220, 210, and 237 dated Jun. 6, 2023 (15 pages).

*Primary Examiner* — Jason-Dennis N Stewart
(74) *Attorney, Agent, or Firm* — BLAIR WALKER IP SERVICES, LLC

(57) ABSTRACT

An orthopedic knee prosthesis includes a femoral component, a tibial bearing, a tibial component, a first magnetic portion associated with the femoral component and including a first pole having a first pole polarity the first magnetic portion not physically interrupting any articulating portion of the curved medial condyle surface or curved lateral condyle surface, and a second magnetic portion associated with one or both of the tibial bearing and/or the tibial component and including a second pole having a second pole polarity, the second pole polarity the same as the first pole polarity, the second magnetic portion not physically interrupting any articulating portion of the concave medial bearing surface or concave lateral bearing surface, wherein the first pole and the second pole are in sufficient proximity to each other such that a magnetic repulsive force is present therebetween.

7 Claims, 18 Drawing Sheets

(56) References Cited

U.S. PATENT DOCUMENTS

| | | |
|---|---|---|
| 6,599,321 B2 | 7/2003 | Hyde, Jr. |
| 7,708,740 B1 | 5/2010 | Bonutti |
| 8,029,570 B2 | 10/2011 | Barnes et al. |
| 8,273,130 B2 | 9/2012 | Gradl |
| 9,757,585 B2 | 9/2017 | Bonutti et al. |
| 10,022,236 B2 | 7/2018 | Ochi |
| 10,478,307 B2 | 11/2019 | Wasielewski et al. |
| 10,660,674 B2 | 5/2020 | Cook et al. |
| 2007/0233251 A1 | 10/2007 | Abdou |
| 2010/0145464 A1 | 6/2010 | Sidhom |
| 2013/0123787 A1 | 5/2013 | Wilkinson |
| 2018/0325682 A1* | 11/2018 | Heldreth ............... A61F 2/389 |
| 2020/0069428 A1 | 3/2020 | Johnson |
| 2022/0069428 A1 | 3/2022 | Chang et al. |

\* cited by examiner

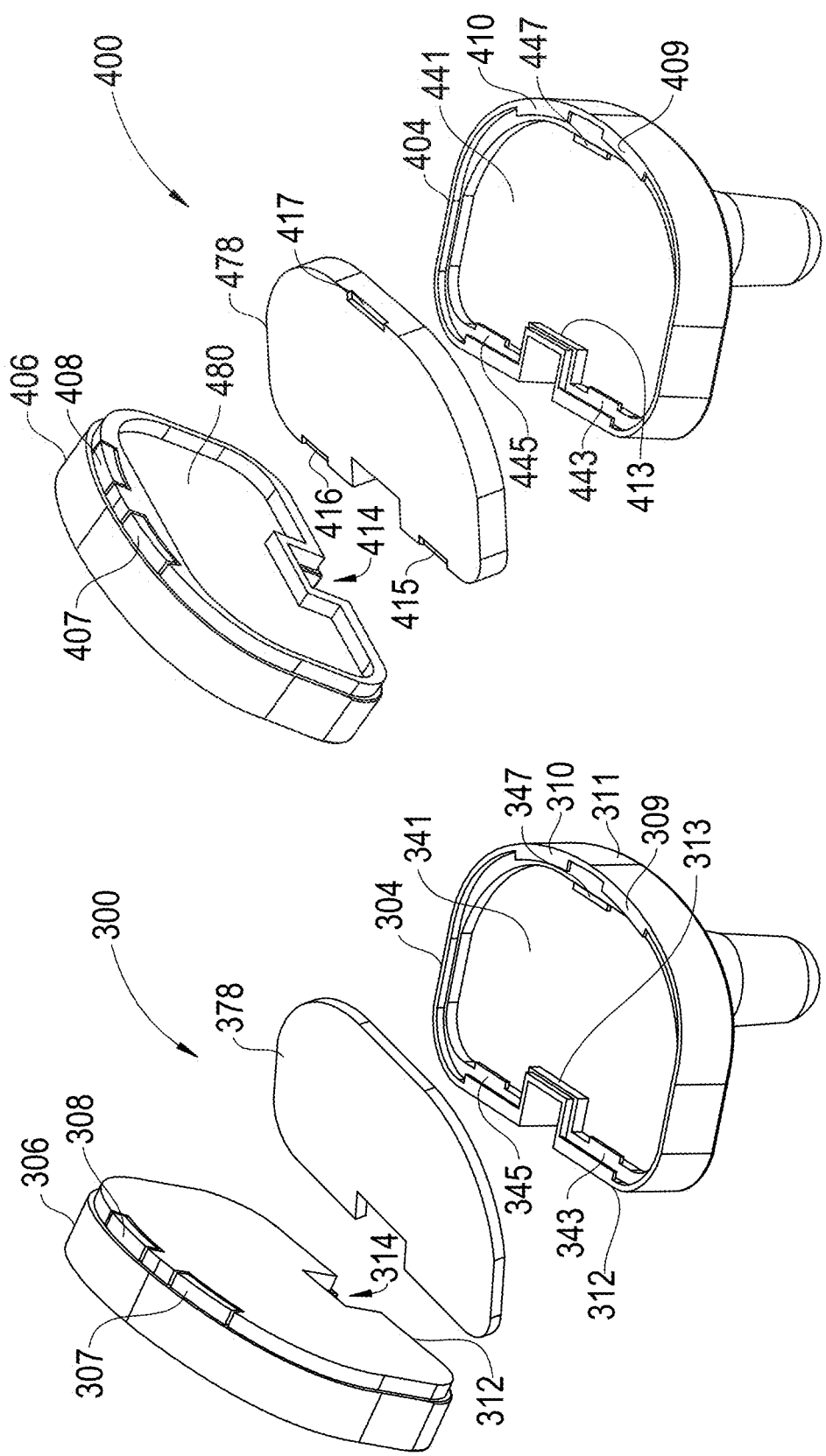

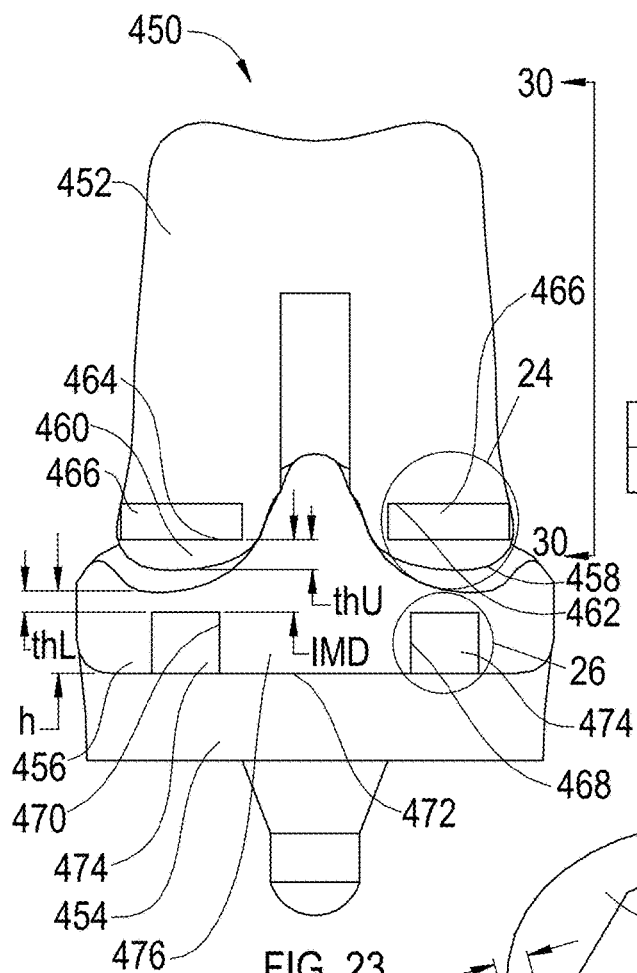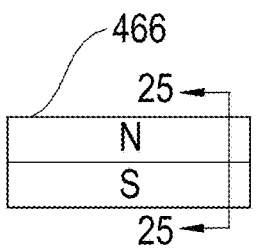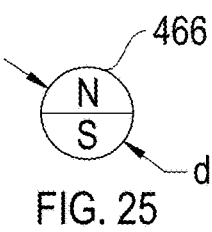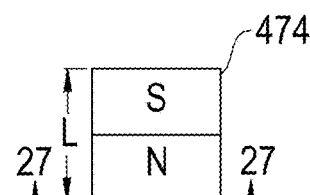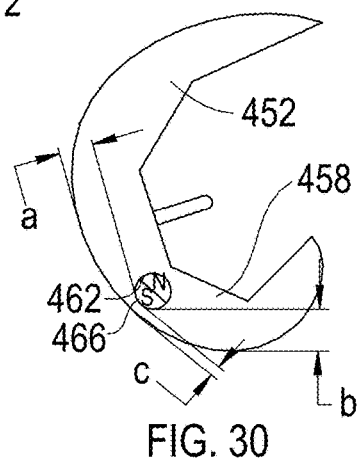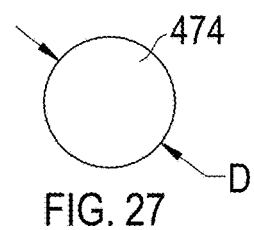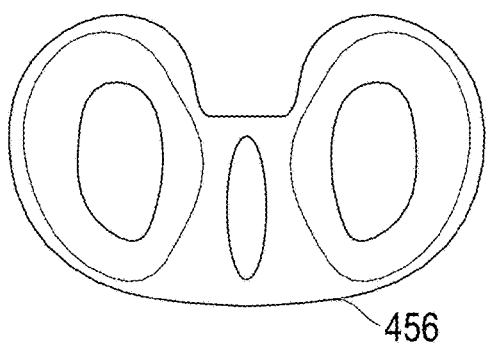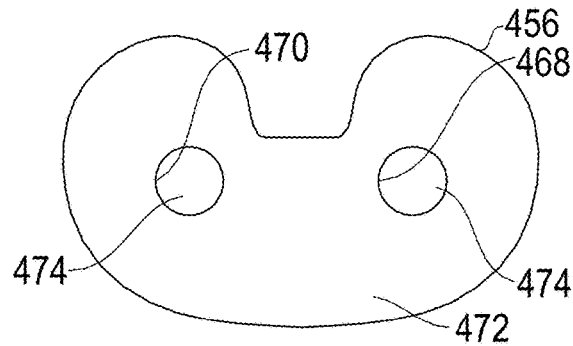

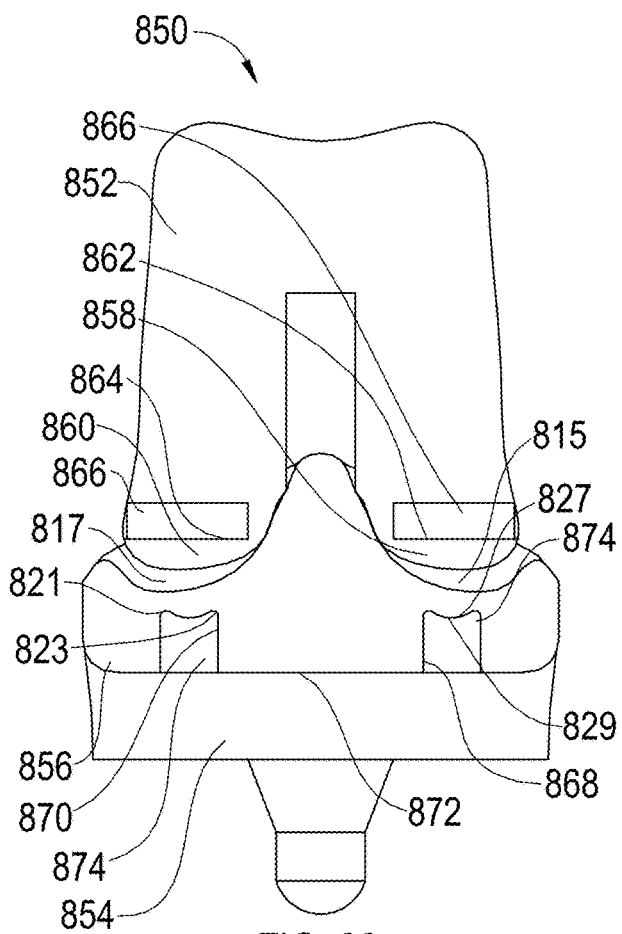
FIG. 39
FIG. 40
FIG. 41
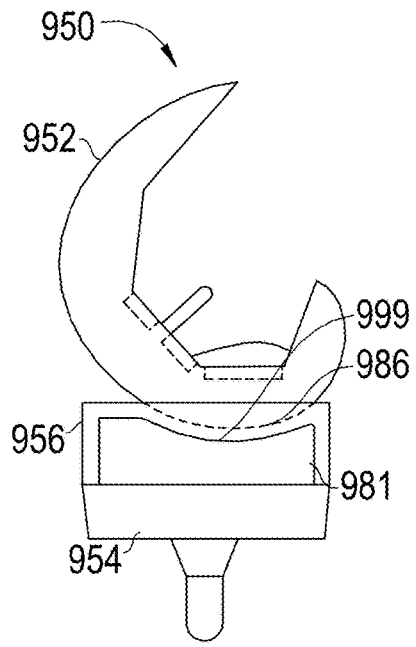
FIG. 42
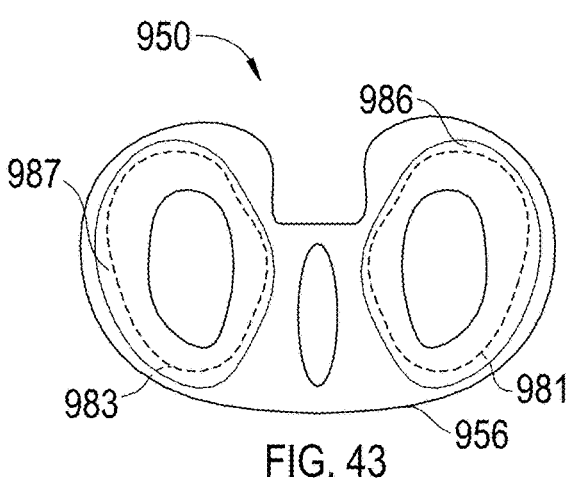
FIG. 43

SYSTEMS AND METHODS FOR MAGNETIC JOINTS

BACKGROUND OF THE INVENTION

Field of the Invention

The field of the invention generally relates to prostheses or artificial substitutes or replacements for parts of the body, such as joints, including but not limited to knees, such as total artificial knee prostheses, or the hip, such as hip prostheses.

SUMMARY OF THE INVENTION

In a first embodiment of the present disclosure, an orthopedic knee prosthesis includes a femoral component including a top portion including a femoral coupler configured to couple to a lower portion of a femur, and a bottom portion including a curved medial condyle surface and a curved lateral condyle surface, a tibial bearing including a top portion including a concave medial bearing surface configured to articulate with the curved medial condyle surface and a concave lateral bearing surface configured to articulate with the curved lateral condyle surface, a tibial component including a bearing coupler configured to couple to the tibial bearing and a bottom portion including a tibial coupler configured to couple to an upper portion of a tibia, a first magnetic portion associated with the femoral component and including a first pole having a first pole polarity, the first magnetic portion not physically interrupting any articulating portion of the curved medial condyle surface and not physically interrupting any articulating portion of the curved lateral condyle surface, and a second magnetic portion associated with one or both of the tibial bearing and/or the tibial component and including a second pole having a second pole polarity, the second pole polarity the same as the first pole polarity, the second magnetic portion not physically interrupting any articulating portion of the concave medial bearing surface and not physically interrupting any articulating portion of the concave lateral bearing surface, wherein, when the curved medial condyle surface is articulatably coupled to the concave medial bearing surface and the curved lateral condyle surface is articulatably coupled to the concave lateral bearing surface, the first pole and the second pole are in sufficient proximity to each other such that a magnetic repulsive force is present, the repulsive force configured to subtract from compressive forces that are applied between the femoral component and the tibial bearing.

In another embodiment of the present disclosure, method for performing a total knee arthroplasty includes providing an orthopedic knee prosthesis including a femoral component including a top portion including a femoral coupler configured to couple to a lower portion of a femur, and a bottom portion including a curved medial condyle surface and a curved lateral condyle surface, a tibial bearing including a top portion including a concave medial bearing surface configured to articulate with the curved medial condyle surface and a concave lateral bearing surface configured to articulate with the curved lateral condyle surface, a tibial component including a bearing coupler configured to couple to the tibial bearing and a bottom portion including a tibial coupler configured to couple to an upper portion of a tibia, a first magnetic portion associated with the femoral component and including a first pole having a first pole polarity, the first magnetic portion not physically interrupting any articulating portion of the curved medial condyle surface and not physically interrupting any articulating portion of the curved lateral condyle surface, and a second magnetic portion associated with one or both of the tibial bearing and/or the tibial component and including a second pole having a second pole polarity, the second pole polarity the same as the first pole polarity, the second magnetic portion not physically interrupting any articulating portion of the concave medial bearing surface and not physically interrupting any articulating portion of the concave lateral bearing surface, wherein, when the curved medial condyle surface is articulatably coupled to the concave medial bearing surface and the curved lateral condyle surface is articulatably coupled to the concave lateral bearing surface, the first pole and the second pole are in sufficient proximity to each other such that a magnetic repulsive force is present, the repulsive force configured to subtract from compressive forces that are applied between the femoral component and the tibial bearing, coupling the femoral coupler to a portion of a femur bone of a patient, coupling the tibial coupler to a portion of a tibia bone of a patient, coupling the tibial component to the tibial bearing, and coupling the femoral component in articulation with the tibial bearing, such that the first pole and the second pole are in sufficient proximity to each other such that a magnetic repulsive force is present.

In yet another embodiment of the present disclosure an orthopedic knee prosthesis includes a femoral component having a top portion and a bottom portion, the femoral component including a femoral coupler configured to couple to a lower portion of a femur, the bottom portion including a curved medial condyle surface and a curved lateral condyle surface, a tibial bearing having a top portion including: a concave medial bearing surface configured to articulate with the curved medial condyle surface, and a concave lateral bearing surface configured to articulate with the curved lateral condyle surface, a tibial component having a bottom portion and a top portion, the bottom portion including a tibial coupler configured to couple to an upper portion of a tibia, the top portion including a tibial bearing coupler configured to couple to the tibial bearing, a first magnetic portion associated with the femoral component and configured to be in proximity to at least a portion of at least one of the curved medial condyle surface or the curved lateral condyle surface, the first magnetic portion having a first pole and a second pole, the second pole having the opposite polarity of the first pole, and a second magnetic portion associated with one or both of the tibial bearing and/or the tibial component and configured to be in proximity to at least a portion of at least one of the concave medial bearing surface or the concave lateral bearing surface, the second magnetic portion having a third pole and a fourth pole, the fourth pole having the opposite polarity of the third pole, wherein the third pole has the same polarity as the first pole, and wherein when (a) the tibial bearing is coupled to the tibial component and (b) the concave bearing surface articulates with the curved condyle surface: the third pole is configured to substantially oppose the first pole in sufficient proximity to thereby produce a first repulsive force.

In still another embodiment of the present disclosure, an orthopedic knee prosthesis includes a femoral component having a top portion and a bottom portion, the femoral component including a femoral coupler configured to couple to a lower portion of a femur, the bottom portion including a curved medial condyle surface and a curved lateral condyle surface, a tibial bearing having a top portion including: a concave medial bearing surface configured to articulate with the curved medial condyle surface, and a concave lateral bearing surface configured to articulate with the curved lateral condyle surface, a tibial component having a bottom portion and a top portion, the bottom portion including a tibial coupler configured to couple to an upper portion of a tibia, the top portion including a tibial bearing coupler configured to couple to the tibial bearing, a first magnetic portion associated with the femoral component and configured to be in proximity to at least a portion of the of the curved medial condyle surface, the first magnetic portion having a first pole and a second pole, the second pole having the opposite polarity of the first pole, a second magnetic portion associated with the femoral component and configured to be in proximity to at least a portion of the of the curved lateral condyle surface, the second magnetic portion having a third pole and a fourth pole, the fourth pole having the opposite polarity of the third pole, a third magnetic portion associated with one or both of the tibial bearing and/or the tibial component and configured to be in proximity to at least a portion of the concave medial bearing surface, the third magnetic portion having a fifth pole and a sixth pole, the sixth pole having the opposite polarity of the fifth pole, and a fourth magnetic portion associated with one or both of the tibial bearing and/or the tibial component and configured to be in proximity to at least a portion of the concave lateral bearing surface, the fourth magnetic portion having a seventh pole and an eighth pole, the eighth pole having the opposite polarity of the seventh pole, and wherein when (a) the tibial bearing is coupled to the tibial component, (b) the concave medial bearing surface articulates with the curved medial condyle surface, and (c) the concave lateral bearing surface articulates with the curved lateral condyle surface: the fifth pole is configured to substantially oppose the first pole in sufficient proximity to thereby produce a first repulsive force and the seventh pole is configured to substantially oppose the third pole in sufficient proximity to thereby produce a second repulsive force.

BRIEF DESCRIPTION OF THE DRAWINGS

FIG. 15 is an exploded view of an alternative embodiment of a tibial portion of a magnetic total knee prosthesis, according to an embodiment of the present disclosure.

FIG. 16 is an exploded view of an alternative embodiment of a tibial portion of a magnetic total knee prosthesis, according to an embodiment of the present disclosure.

FIG. 23 is a front view of a magnetic total knee prosthesis, according to an alternative embodiment of the present disclosure.

FIG. 24 is a detail view of a femoral component magnet of the prosthesis of FIG. 23 taken from circle 24.

FIG. 25 is a cross-sectional view of the magnet of FIG. 24 taken from line 25-25.

FIG. 26 is a detail view of a tibial bearing magnet of the prosthesis of FIG. 23 taken from circle 26.

FIG. 27 is a cross-sectional view of the magnet of FIG. 26 taken from line 27-27.

FIG. 28 is a top view of the tibial bearing of FIG. 23.

FIG. 29 is a bottom view of the tibial bearing of FIG. 23.

FIG. 30 is a side view of the femoral component of the prosthesis of FIG. 23 taken from line 30-30.

FIG. 39 front view of a magnetic total knee prosthesis, according to an alternative embodiment of the present disclosure.

FIG. 40 is a perspective view of a magnet of the magnetic total knee prosthesis of FIG. 39.

FIG. 41 is a top view of a tibial bearing of a magnetic total knee prosthesis, according to an embodiment of the present disclosure.

FIG. 42 is a side view of a magnetic total knee prosthesis, according to an embodiment of the present disclosure.

FIG. 43 is a top view of the tibial bearing of FIG. 42.

DETAILED DESCRIPTION OF THE ILLUSTRATED EMBODIMENTS

Figure 1:
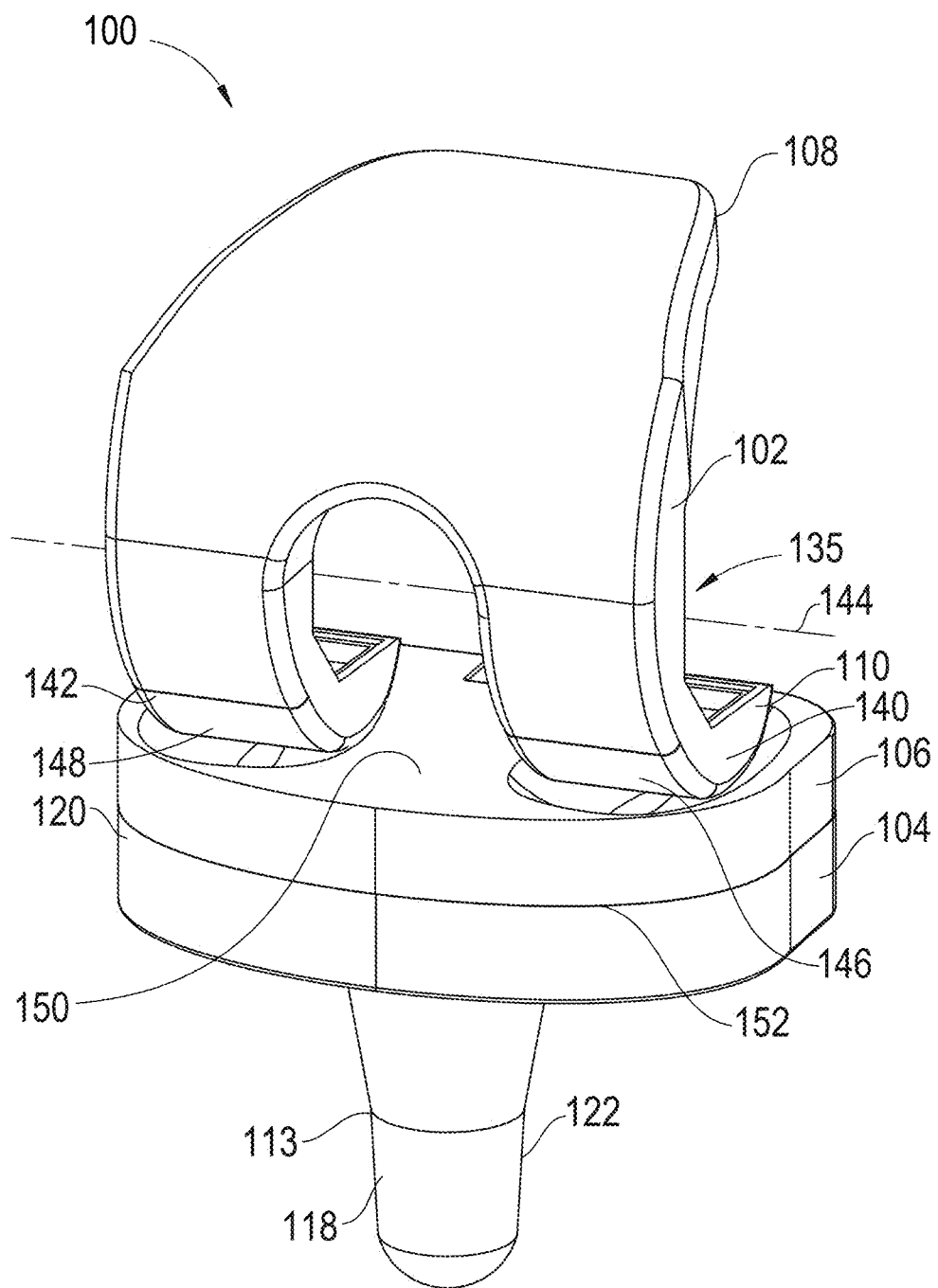
FIG. 1 is a front perspective view of a magnetic total knee prosthesis according to an embodiment of the present disclosure.

Total knee arthroplasty, or total knee replacement, has undergone many mechanical advancements over the past several decades. However, many problems regarding patient function and patient satisfaction have as yet not been addressed with appropriate solutions. A crucial concept that has not been sufficiently addressed is the transition between the weight bearing surfaces of the femoral and tibial sides of the articulation of total knee prostheses. Experience in joint arthroplasty surgery over several decades, often involving special fellowship training, has enhanced surgeons' capacity to perform complex joint reconstructive procedures. Many of these procedures are now guided by computer systems and robotic equipment.

However, despite these advances, a glaring, monumental problem still remains. The normal, natural functioning knee joint has a complex arrangement of surface lining, specialized joint fluid, and multiple cartilaginous structures whose physical characteristics and interplay play an important part in the natural function of the knee. Much of the biomechanical characteristics of these natural elements have not been included in total knee prosthesis designs. In recent years, these functional characteristics have been overlooked, as the generational improvement of total knee prostheses focuses instead on other, arguably more minor, changes.

The surface of a natural knee joint is a smooth, glistening layer possessing a complex combination of water, chondrocytes, extracellular matrix, collagens, proteoglycans, and other substances. These and other biological structures of the knee, and their functionality, have been largely ignored in the construction of total knee prostheses. Not surprisingly, most patients receiving total knee prostheses in total knee arthroplasty procedures later opine that their knees "do not feel normal." Many surgeons tell their patients that about a year after the replacement surgery, the knee will start to feel "normal." However, it has been reported that this is not truly the case. The memory of the fluid feel during walking, running, dancing, jumping, and even standing, when the person possessed two normal, natural knee joints, remains within the mind of a total knee patient. This memory is longstanding, and serves as a stark comparison to the unnatural feel the patient is suddenly stuck with following total knee replacement surgery. This is true whether the replacement involved one knee, or both knees, and whether it involved one surgery or more than one surgery. Artificial total knee joints typically comprise a metal femoral component configured to be coupled to the patient's femur, a metal tibial component configured to be coupled to the patient's tibia, and a polymeric tibial bearing configured to be coupled to the tibial component and configured to articulate with the femoral component. The metal components can comprise Cobalt-Chromium (CoCr) alloys, which can comprise nickel. The polymeric bearing can comprise polyethylene, such as ultra-high molecular weight polyethylene (UEMWPE) or highly-cross-linked polyethylene (HXLPE). Though these components allow for the flex between the patient's tibia and femur, as well as a certain amount of torsional freedom, the bearing surfaces are highly rigid, with much less elastic compression or spring action than that provided by the naturally-occurring substances in the knee. The Applicant has determined that many of these somewhat complex mechanical differences are important reasons for the fleeting or entirely absent natural feel of total knee prostheses. It is reported that water makes up between about 65% and about 80% of cartilage. Articular cartilage and meniscal cartilage, as well as viscous joint fluid are some of the naturally-occurring materials that control the fine mechanical performance of a healthy knee. There is no true comparative simulation of this in the metal and polymeric materials of the current total knee prostheses.

The total knee prostheses presented herein include embodiments comprising a magnetic joint which is configured to add back some of these previously-removed and missing mechanical complexities. By incorporating one or more opposing, distance-dependent forces based on magnetic repulsion into the prosthesis, the magnetic total knee prosthesis provides the patient with a more natural feel that was absent in previous total knee prostheses. In some cases, these additional forces may take the place of the viscoelastic "adherence" effect experienced in normal healthy joints having synovial fluid. The natural feel may allow a more comfortable stroll through an uneven or hilly path in some cases, or may even allow running to be possible where it otherwise would not have been. This capability provided by the magnetic total knee prosthesis exists because of the increase in balance, increase in dexterity, and/or reduction in pain. In some cases, a complete removal of pain is possible.

Further benefits from the addition of the magnetically-provided repulsion (repulsive, repelling) forces include: decreased normal forces, and thus decreased frictional forces, between the components of the prosthesis/implant, for example, between the femoral component and the tibial bearing. As such, wear between the implant components is decreased. As a result, less particulate is created, for example, particulate that may be shed from the polymeric tibial bearing. Furthermore, an overall "gliding" motion between the implant components is created. Along with decreased wear is less generated heat, and less unnatural application of forces on bone, cartilage, tendon, ligament, nerves, and other soft tissue. Other problems associated with joint replacement surgery may also be significantly mitigated, such as fracture of the components, dislocation of the components, asymmetric wear of the components, or fracture of the bones (e.g., tibia, femur), or damage to other tissue that surround the components. The magnetic fields that are formed to create the repelling forces help, thus, to simulate the biological structures that are no longer present in the artificial joint. Besides the knee joint, other joints can be aided by the teaching herein, such as other weight-bearing joints like the hip joint, ankle joint, or vertebral joints, or even more intermittent weight-bearing joints such as the shoulder joint, elbow joint, wrist, or even spinal column. The improvements described herein address many general challenges caused by impact, acceleration, and deceleration. The magnetically-created adjunctive forces in the embodiments taught herein serve to bridge the gap between the non-biologic and the biologic portions of the leg having an artificial knee prosthesis.

Figure 2:
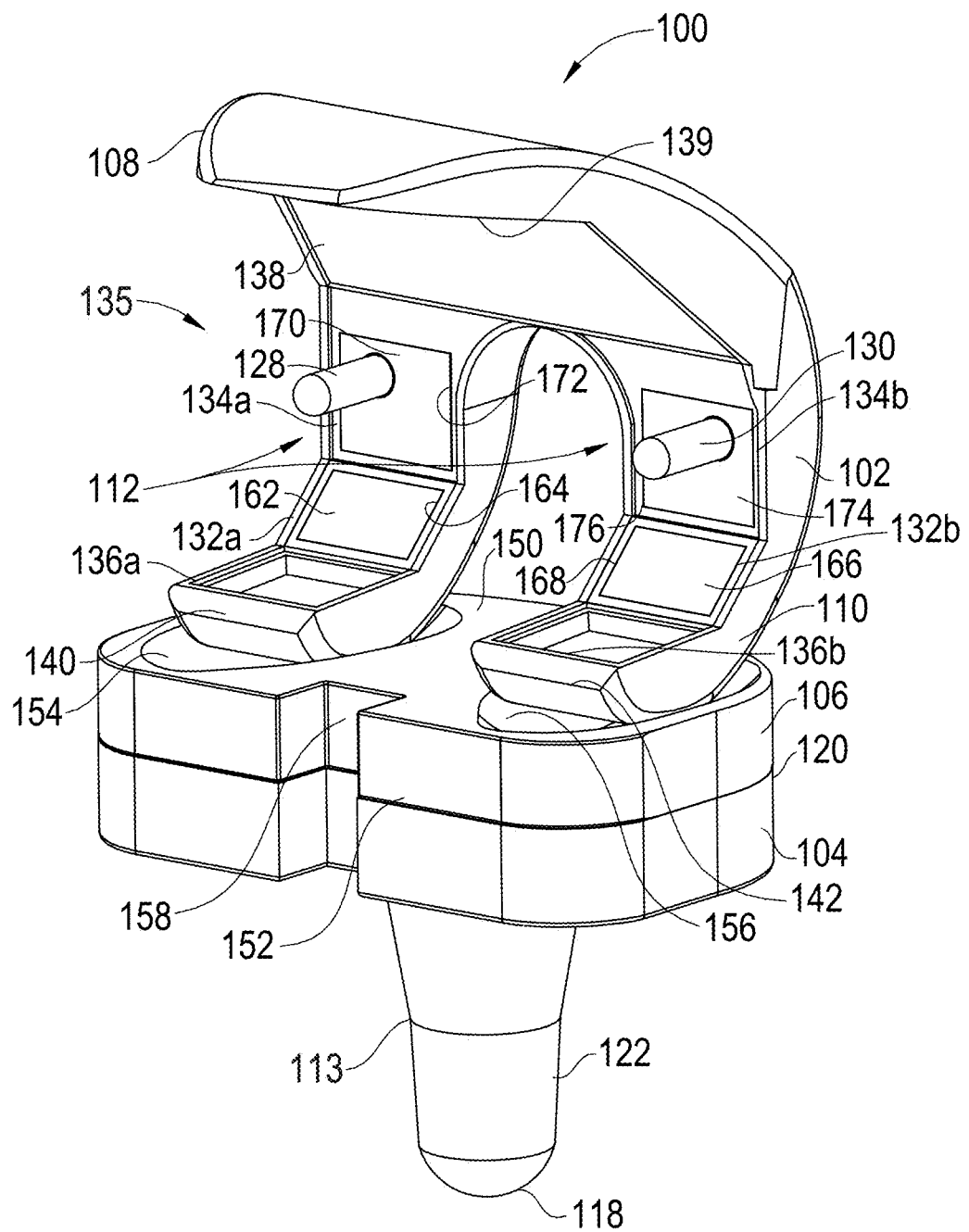
FIG. 2 is a rear perspective view of the prosthesis of FIG. 1.
Figure 3:
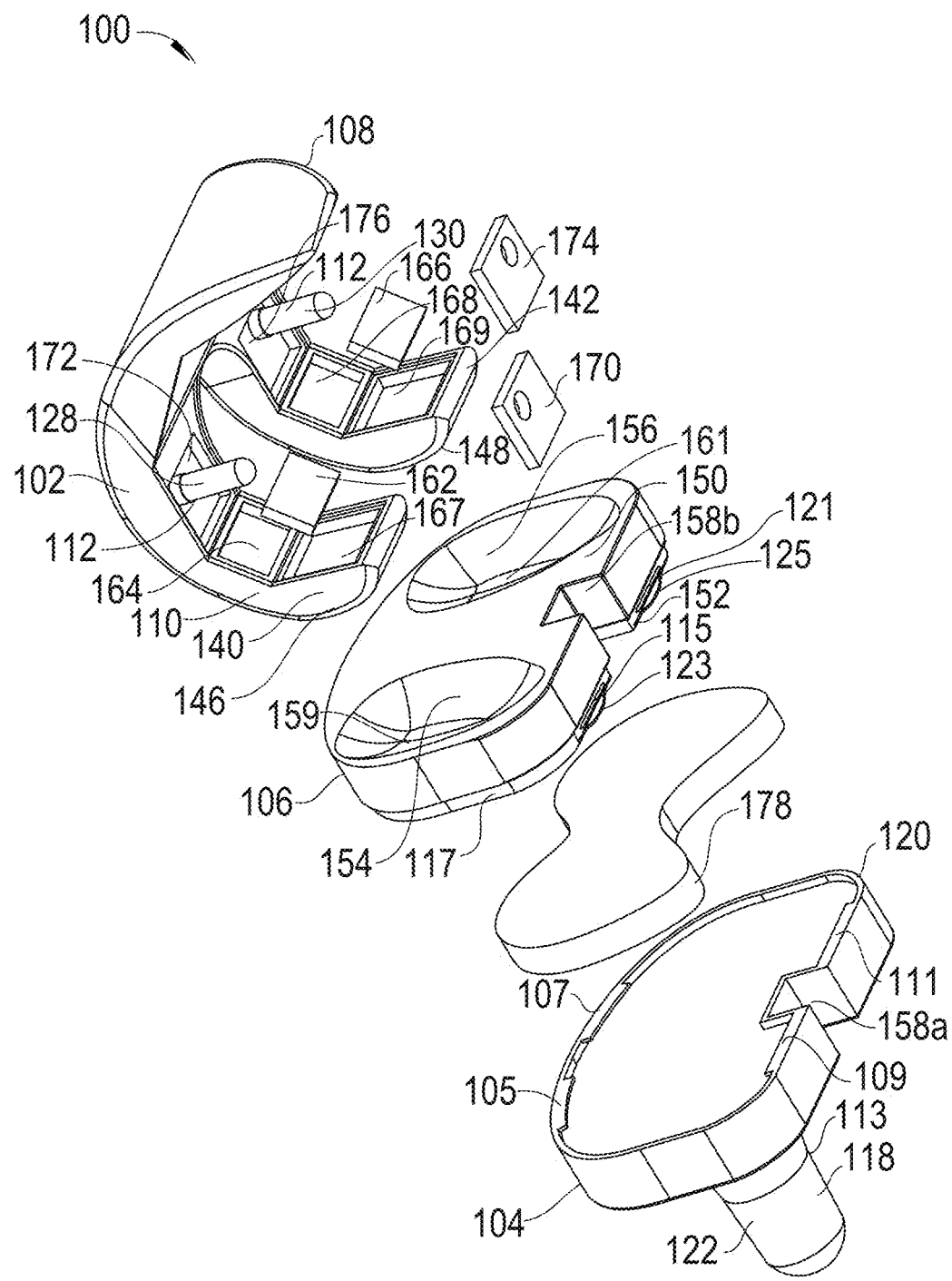
FIG. 3 is a first exploded view of the prosthesis of FIG. 1.
Figure 22:
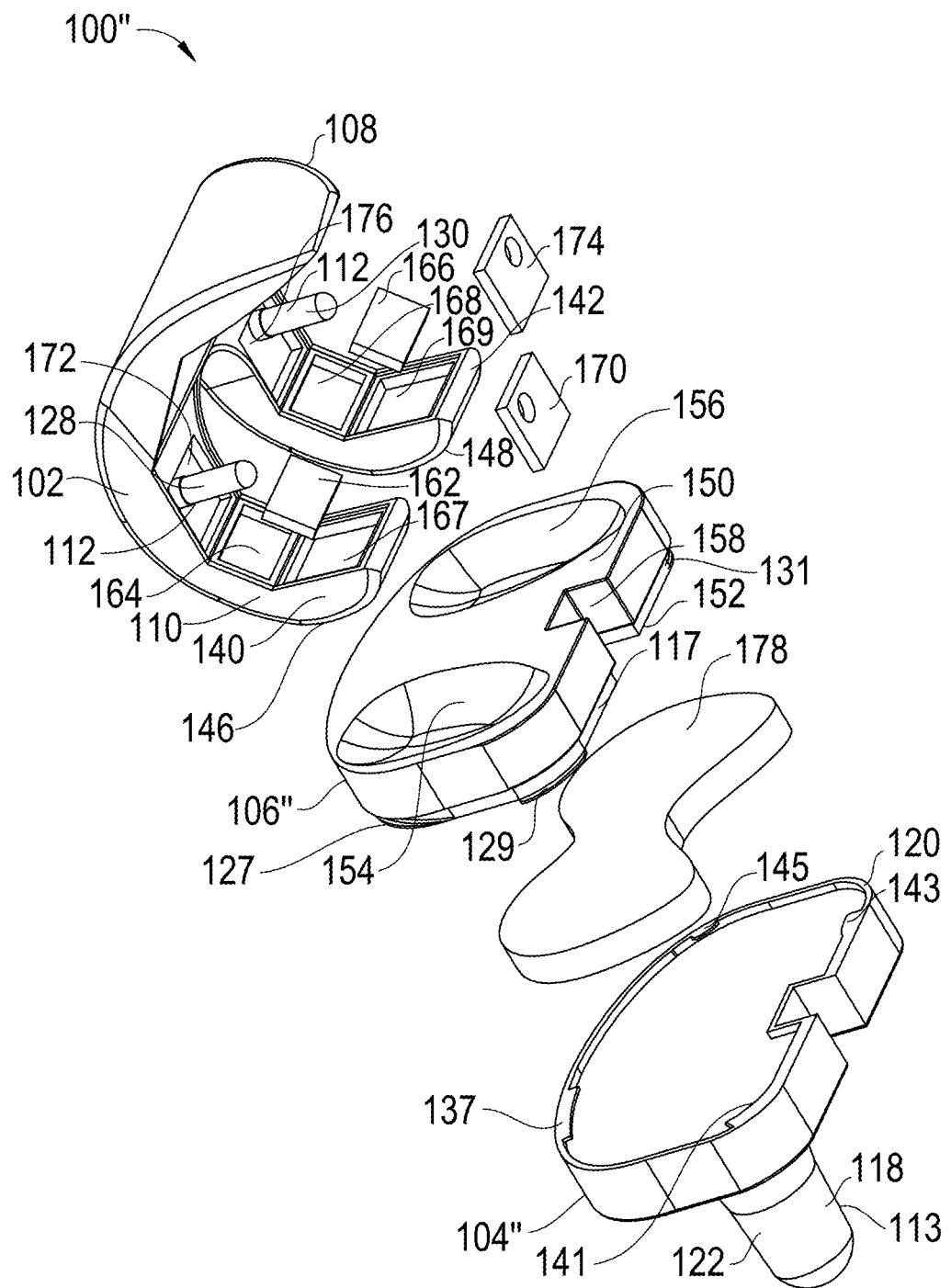
FIG. 22 is an exploded view of a magnetic total knee prosthesis, according to an alternative embodiment of the present disclosure.

FIGS. 1-7 illustrate a magnetic total knee prosthesis 100 configured to be implanted within a patient 1 (FIG. 5) during a total knee arthroplasty surgery. The magnetic total knee prosthesis 100 comprises a femoral component 102, a tibial component 104, and a tibial bearing 106. The femoral component 102 and the tibial component 104 can each comprise a metal or metal alloy, for example a cobalt chromium alloy. The tibial bearing 106 can comprise a polymer, such as polyethylene. In some embodiments, the tibial bearing 106 comprises ultra-high molecular weight polyethylene (UHMWPE). In some embodiments, the tibial bearing 106 comprises highly cross-linker polyethylene (HXLPE). In some embodiments the tibial bearing 106 is configured to be screwed into the tibial component 104. For example, the tibial bearing 106 and the tibial component 104 can each have cooperative threading configured to allow their screwable attachment to each other (FIG. 22). In other embodiments, the tibial bearing 106 is configured to snap into the tibial component 104. For example, snaps 105, 107, 109, 111 in the tibial component 104 (FIG. 3) are configured to snappingly engage with the perimeter 117 of the tibial bearing 106. Furthermore, snaps 101, 103 in the tibial bearing 106 (FIG. 4) are configured to snappingly engage with the perimeter 119 if of the tibial component 104. The perimeters 117, 119 can each include undercuts 115, 121 (FIG. 3), configured to allow any of the snaps 101, 103, 105, 107, 109, 111 to snap therein. In FIG. 3, the undercut 115 on the perimeter 117 is configured to releasably snap with snap 109 and the undercut 121 on the perimeter 117 is configured to releasably snap with snap 111. The undercut 115 can be axially adjacent a tab 123, extending from the perimeter 117, and the undercut 121 can be axially adjacent a tab 125, extending from the perimeter 117. In some embodiments the tabs 123, 125 can be configured to be substantially flexible to allow a fully axial snap to occur. In some embodiments, a lower and/or upper portion of the tabs 123, 125 can include a taper or lead in, in order to minimize the stress during snapping and/or unsnapping. Having the snappable portions unsnappable allows for more adaptability during surgery preparation and even during the surgery itself, as multiple combinations of components can be trialed.

Figure 4:
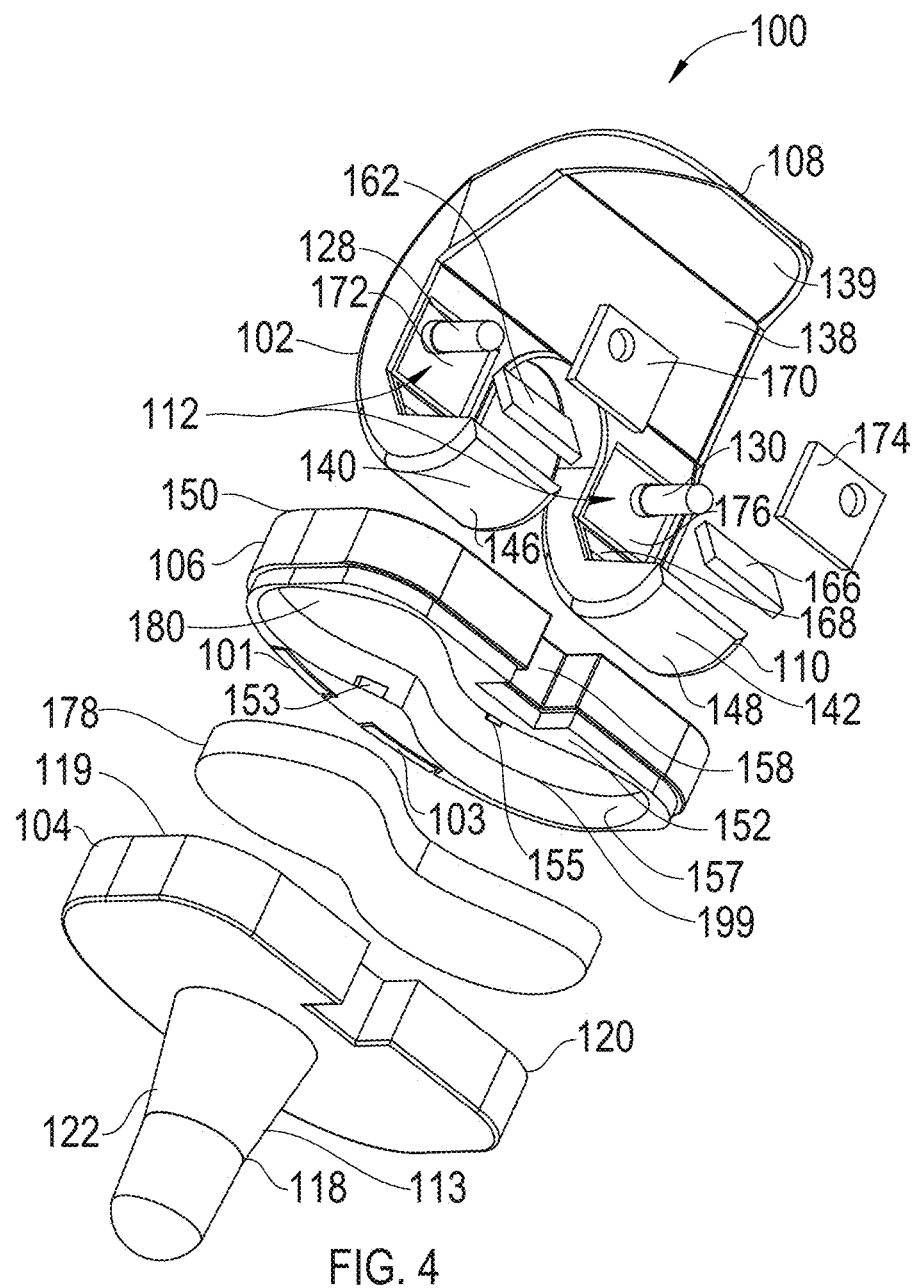
FIG. 4 is a second exploded view of the prosthesis of FIG. 1.
Figure 5:
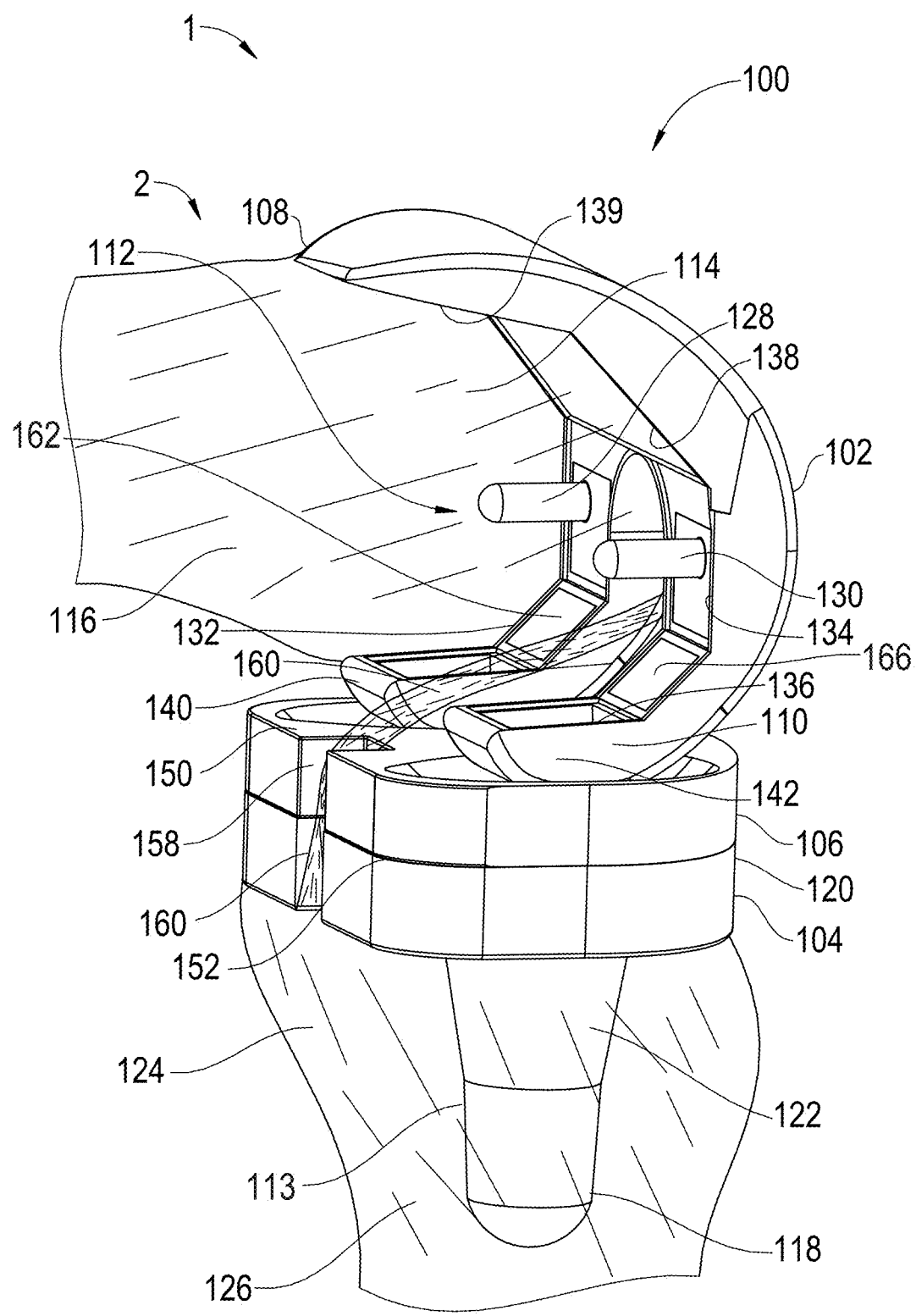
FIG. 5 is a perspective view of the prosthesis in a first position as implanted within a patient, according to an embodiment of the present disclosure.
Figure 6:
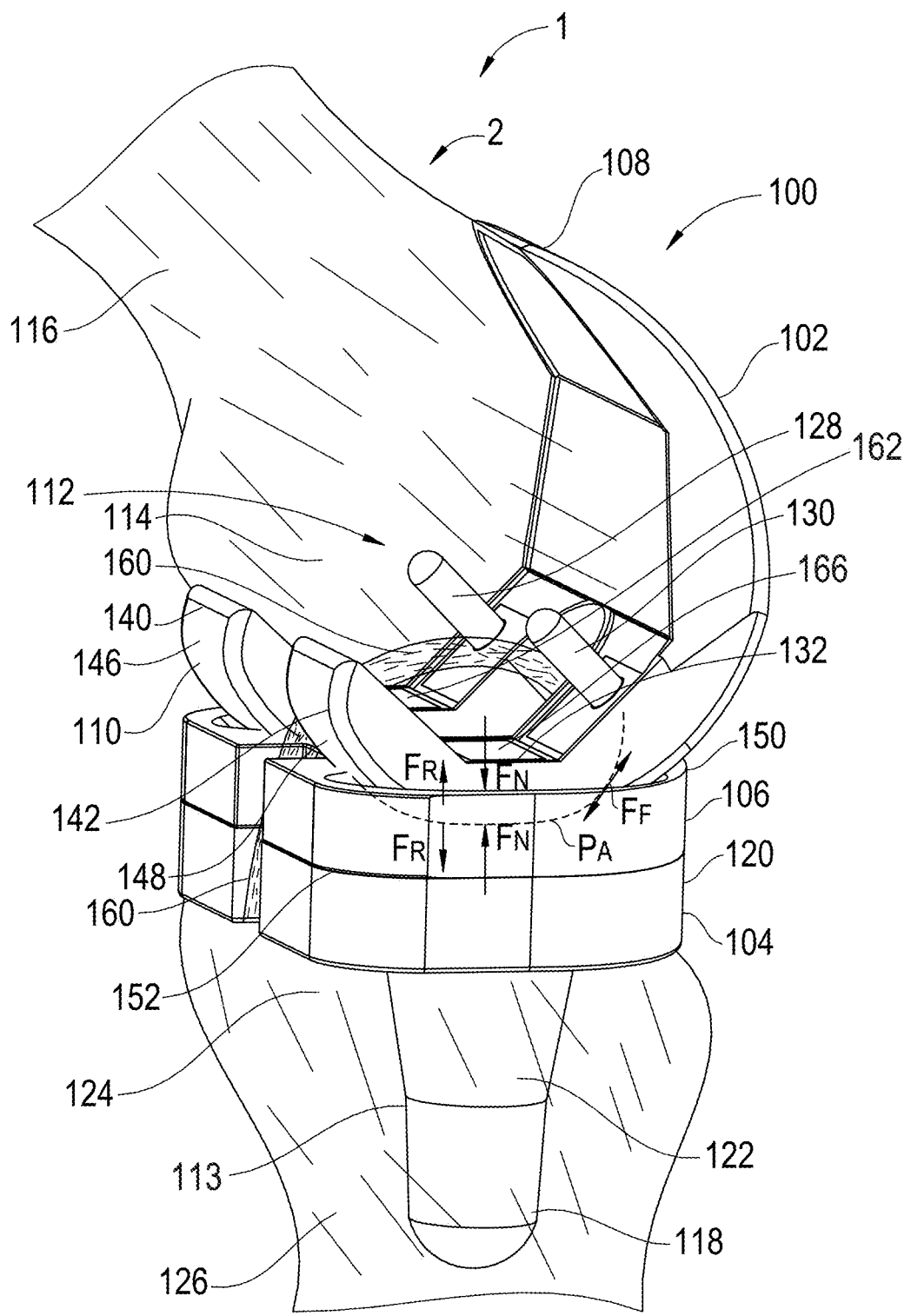
FIG. 6 is a perspective view of the prosthesis in a second position as implanted within a patient, according to an embodiment of the present disclosure.
Figure 7:
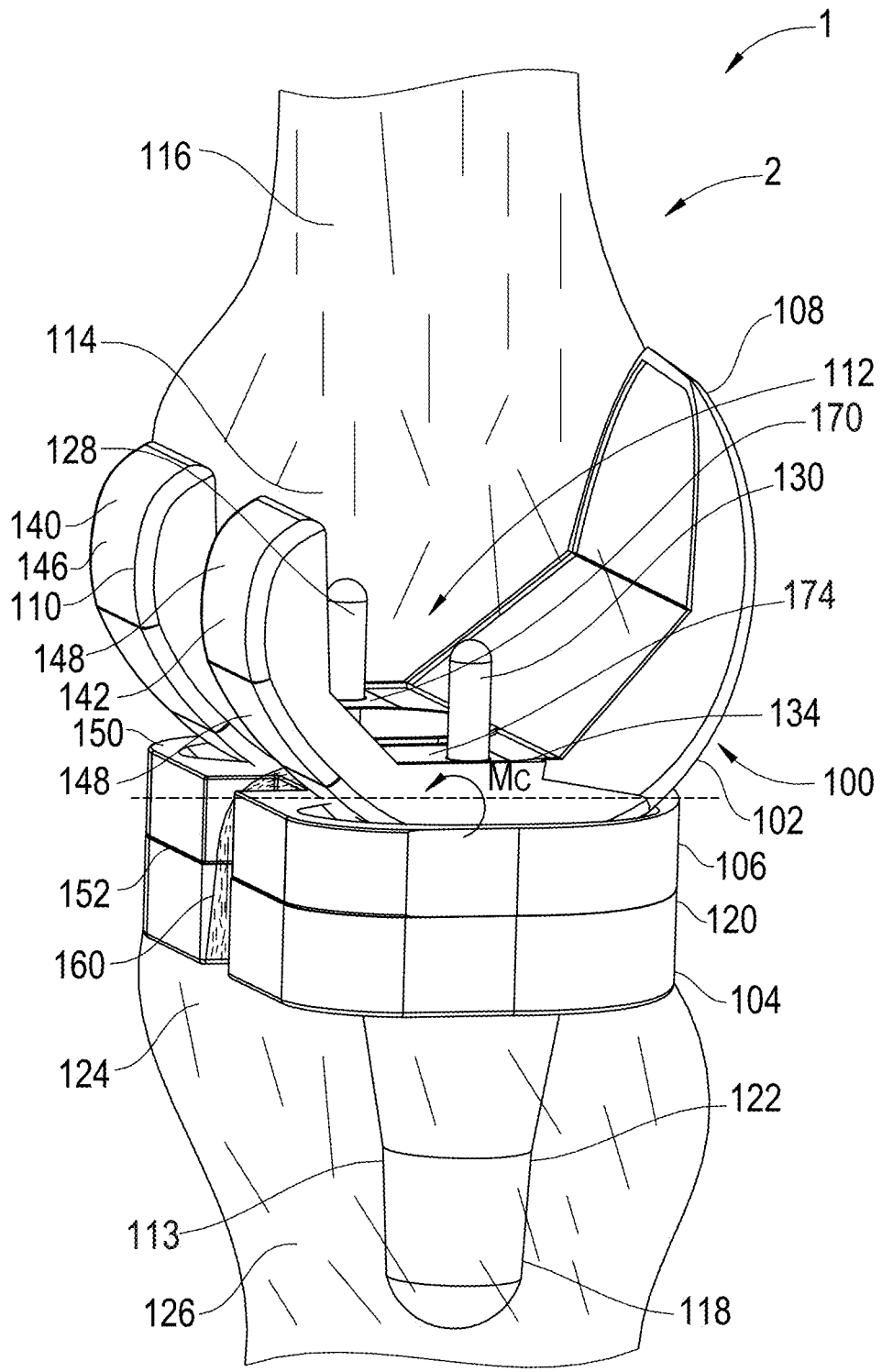
FIG. 7 is a perspective view of the prosthesis in a third position as implanted within a patient, according to an embodiment of the present disclosure.

The femoral component 102 comprises a top portion 108 and a bottom portion 110. The top portion 108 and/or bottom portion 110 include a femoral coupler 112 configured to be coupled to a lower portion 114 of a femur 116 (FIGS. 5-7). The tibial component 104 comprises a bottom portion 118 and a top portion 120. The bottom portion 118 includes a tibial coupler 122 configured to be coupled to an upper portion 124 of a tibia 126 (FIGS. 5-7). The femoral coupler 112 comprises a first peg 128 and a second peg 130 configured for compatibility and adherence to bone. The femoral coupler 112 further comprises pairs of first 132a/132b, second 134a/134b, third 136a/136b faces, a fourth face 138, and a fifth face 139, each pair 132, 134, 136 non-parallel to the others (FIG. 2). The faces 132, 134, 136, 138, 139 are configured to extend around the lower portion 114 of the femur 116. The tibial coupler 122 includes a stem 113, configured for compatibility and adherence to bone. The bottom portion 110 of the femoral component 102 includes a lateral condyle 140 and a medial condyle 142 which each curve around a transverse axis 144 (FIG. 1). The lateral condyle 140 includes a curved lateral condyle surface 146 and the medial condyle 142 includes a curved medial condyle surface 148. The tibial bearing 106 includes a top portion 150 and a bottom portion 152. The top portion 150 of the tibial bearing 106 includes a concave lateral bearing surface 154 and a concave medial bearing surface 156 (FIGS. 2-3). The lateral condyle 140 and the medial condyle 142 are each configured to articulate in a sliding manner along an arcuate path within the concave lateral bearing surface 154 and the concave medial bearing surface 156, respectively. Specifically, the curved lateral condyle surface 146 slides over the concave lateral bearing surface 154 and the curved medial condyle surface 148 slides over the concave medial bearing surface 156, while the femoral component 102 changes its relative rotational orientation in relation to the tibial bearing 106 (and thus in relation to the tibial component 104). In the embodiment illustrated in FIG. 1, the change in rotational orientation is in relation to the transverse axis 144. Thus, the rotational axis and the transverse axis 144 are colinear. In other embodiments, the rotational axis can be different from the transverse axis 144 but it parallel to the transverse axis 144. In some embodiments the rotational axis and transverse axis 144 are non-parallel to each other. The magnetic total knee prosthesis 100 depicted in FIGS. 1-7 is intended for the left knee. A right knee model would typically be a mirror image, and thus a reversed copy of all of the teachings presented herein should also be assumed to exist. However, in some embodiments, the right knee and left knee models can be designed to be the same, such that only a single model is needed, as shown in the embodiment of FIGS. 23-30. This may, for example, be applicable in locations with a minimal healthcare budget. In some embodiments, the single model, can be adaptable or easily modifiable in order to configure it for the left knee or right knee.

FIGS. 5-7 illustrate three different positions of the articulation with the magnetic total knee prosthesis 100 implanted within a leg 2 of a patient 1. "Articulation" does not require attachment, though it can include attachment. However, "articulation" may also include simply the condyles 140, 142 movably seated within the tibial bearing 106. The femoral coupler 112 is shown coupled to the femur 116, and the tibial coupler 112 is shown coupled to the tibia 126. Most of the soft tissue of the leg 2 is not shown, for clarity purposes. In the generally 90° flexed position shown in FIG. 5, the faces 136 are adjacent the concave lateral bearing surface 154 and the concave medial bearing surface 156. In the generally 45° semi-flexed position shown in FIG. 6, the faces 132 are adjacent the concave lateral bearing surface 154 and the concave medial bearing surface 156. In the generally 0° extended position shown in FIG. 7, the faces 134 are adjacent the concave lateral bearing surface 154 and the concave medial bearing surface 156. The magnetic total knee prosthesis 100 shown in FIGS. 1-7 is a cruciate retaining knee prosthesis, thus comprising a horizontally-extending space 158 or groove in the tibial component 104 and the tibial bearing 106 configured for the posterior cruciate ligament (PCL) 160 to extend therethrough. The tibial component 104 includes a first groove portion 158a and the tibial bearing 106 comprises a second groove portion 158b (FIG. 3). All of the embodiments of the magnetic total knee prosthesis 100 disclosed herein, including alternative embodiments, can have this "cruciate retaining" configuration. Alternatively, all of the embodiments, can instead have an alternative "posterior stabilized" configuration, featuring a box on the femoral component 102 and a post on the tibial component 104. Alternatively, all of the embodiments can instead be configured with an alternative "anterior stabilized" configuration or with a "bicruciate retaining" (PCL and ACL) configuration.

The faces 132, 134 do not represent fully planar faces on the interior portion 135 (FIGS. 1-2) of the femoral component 102, but instead, each portion comprises a cavity for the placement of a permanent magnet, and a perimeter surrounding the cavity, and approximating the face. Turning to FIGS. 2-4, a first magnet 162 is held within a first rectangular cavity 164, in the lateral condyle 140. A second magnet 166 is held within a second rectangular cavity 168, in the medial condyle 142. A third magnet 170 is held within a third cavity 172, in the lateral condyle 140. And, a fourth magnet 174 is held within a fourth cavity 176, in the medial condyle 142. The cavities 164, 168, 172, 176 each extend from the interior portion 135 of the femoral component 102. A fifth magnet 178 is held within a fifth cavity 180 in the tibial bearing 106 (FIG. 4). The fifth cavity 180 extends an axially depth from the bottom portion 152 of the tibial bearing 106. The magnets 162, 166, 170, 174, 178 can be configured to be snapped into the cavities 164, 168, 172, 176, 180, or can be adhesively, hot melt, or epoxy bonded into the cavities 164, 168, 172, 176, 180. The cavities 164, 168, 172, 176, 180 serve to protect the magnets 162, 166, 170, 174, 178, but also serve to protect the magnetic total knee prosthesis 100 from degradation cause by biological growth (e.g., bone, soft tissue, protein deposits, etc.) or by repetitive use of the knee. The cavities 164, 168, 172, 176, 180 also serve to protect the tissue and overall systems (lymphatic, vascular, nervous, muscular, etc.) from the material of the magnets 162, 166, 170, 174, 178 (as would any magnetic protective coating). Snaps 153, 155 can extend transversely from a perimeter 157 of the fifth cavity 180, and are configured to provide a positive detent or catch to allow the magnet 178 to snap into the fifth cavity 180 (FIG. 4). Turning to FIG. 6, the magnets 162, 166, 170, 174 of the femoral component 102 are configured to cause one or more magnetically-formed repelling forces ($F_R$) with the magnet 178 of the tibial bearing 106. This/these repelling forces are configured to counteract some of the normal forces ($F_N$) between the condyles 140, 142 and the concave bearing surfaces 154, 156, thus decreasing the frictional force ($F_F$) along the arcuate path ($P_A$) of the condyles 140, 142 with respect to the concave bearing surfaces 154, 156. As previously mentioned, the magnetically-created adjunctive forces in the embodiments taught herein serve to bridge the gap between the non-biologic and the biologic portions of the leg having an artificial knee prosthesis. The variable characteristic of a repulsive magnetic field based on orientation, distance, and varied by motion along the arcuate path ($P_A$), adds some "float" into the "feel" of the knee of the patient having an implanted magnetic total knee prosthesis 100.

In the generally 90° flexed position shown in FIG. 5, the magnets 162, 166 are the closest magnets to magnet 178. However, the magnets 162, 166 are farther from the magnet 178 than they are in the generally 45° flexed position shown in FIG. 6. Thus, a smaller magnetically-formed repelling force ($F_R$) would be expected in the FIG. 5 position than in the FIG. 6 position. This is consistent with the physical condition, because a person with 90° flexed legs does not typically place large loads on the legs, this being more of a sitting position. However, the generally 45° position of FIG. 6 and the generally 0° position of FIG. 7 are both common positions during walking and running, and the generally 0° position (or a position between 0° and 45°) is a common position during standing. Thus, the greater proximity (to the magnet 178) of the magnets 162, 166 in the 45° position of FIG. 6 or of the magnets 170, 174 in the 0° position of FIG. 7 would create a larger magnetically-formed repelling force ($F_R$). This is consistent with the needs to somewhat counteract the normal forces ($F_N$) in these positions (dur to some carrying of the weight of the patient's 1 body.

Figure 8:
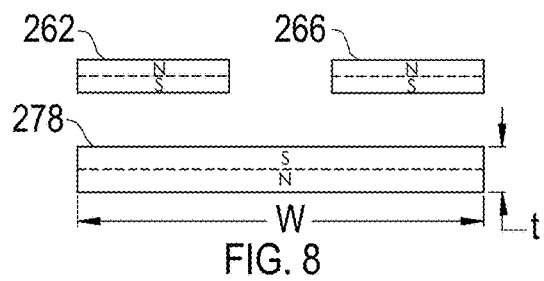
FIG. 8 is a side view of a first configuration between repelling permanent magnets of a prosthesis, according to an embodiment of the present disclosure.

The magnets 162, 166, 170, 174, 178 in the embodiments described herein comprise permanent magnets, however, in alternative embodiments, one of more of the magnets 162, 166, 170, 174, 178 can comprise electromagnets. In a first embodiment of permanent magnet poling shown in FIG. 8, first and second permanent magnets 262, 266 are configured to be secured, respectively, to two condyles of a femoral component. The magnets 262, 262, for example, can be used to construct any of the magnet pairs 162/166 or 170/174 of the femoral component 102 of FIGS. 1-7. Each of the magnets 262, 266 has a north pole N and a south pole S. A permanent magnet 278 can be used to construct the magnet 178 of FIGS. 1-7. The magnet 278 has a north pole N and a south pole S, a width W, and a thickness t. As shown in FIG. 8, the south poles S of the magnets 262, 266 are configured to face the south pole S of the magnet 278, thus utilizing the repulsion of the magnets to each other, or in particular, the repulsion to magnets 262, 266 to magnet 278. This repelling set-up is what forms one or more magnetically-formed repelling forces ($F_R$), as shown in FIG. 6. In some embodiments, the mass, volume, thickness t, and/or overall magnetic field strength of the magnet 262 can be the same as the mass, volume, thickness t, and/or overall magnetic field strength of the magnet 266. However, in alternative embodiments, the mass, volume, thickness t, and/or overall magnetic field strength of the magnet 262 can be greater or less than the mass, volume, thickness t, and/or overall magnetic field strength of the magnet 266, thus allowing the potential of a complex magnetic field that provides an uneven distribution of magnetically-formed repelling forces ($F_R$) between medial and lateral aspects of the artificial knee. This uneven strength between the medial and lateral aspects may be useful in patients having a particular non-standard condition, such as genu varum (bow legs), genu valgum (knock-knees), pronation, supination, in-toeing (pigeon toes), out-toeing (duck footed), or improperly healed bone (e.g., complex or spiral fracture). The permanent magnets may also be considered magnetic shims, and can be available to the user in a number of different thicknesses. Choosing a certain thickness of magnetic shim can allow the magnet to be flush with the remainder of the implant (e.g., flush with one or more of the faces). Alternatively, the user can choose a thickness of the magnetic shim such that the magnets are configured to be sub-flush.

Figure 9:
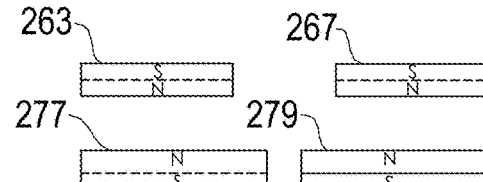
FIG. 9 is a side view of a second configuration between repelling permanent magnets of a prosthesis, according to an embodiment of the present disclosure.

FIG. 9 illustrates yet another permanent magnet configuration and polling design. The first and second permanent magnets 263, 267 can be used to construct any of the magnet pairs 162/166 or 170/174 of the femoral component 102 of FIGS. 1-7. The third and fourth permanent magnets 277, 279 together replace the single permanent magnet 178 or single permanent magnet 278. The magnet 263 is configured to substantially interface with the magnet 277. The magnet 267 is configured to substantially interface with the magnet 279. The north poles N of the magnets 263, 267 are configured to substantially face the north poles N of the magnets 277, 279, respectively, thus utilizing the repulsion of the magnets to each other to form one or more magnetically-formed repelling forces ($F_R$), as shown in FIG. 6. There may be some repulsive effect between magnet 263 and magnet 279, or between magnet 267 and magnet 277, but the repulsion between magnet 263 and magnet 277 and the repulsion between magnet 267 and magnet 279 generally dominate. In some embodiments, the mass, volume, thickness t (see FIG. 8), and/or overall magnetic field strength of the magnet 263 can be the same as the mass, volume, thickness t, and/or overall magnetic field strength of the magnet 267, and the mass, volume, thickness t, and/or overall magnetic field strength of the magnet 277 can be the same as the mass, volume, thickness t, and/or overall magnetic field strength of the magnet 279. However, in alternative embodiments, the mass, volume, thickness t, and/or overall magnetic field strength of the magnet 263 can be greater or less than the mass, volume, thickness t, and/or overall magnetic field strength of the magnet 267, thus allowing the potential of a complex magnetic field that provides an uneven distribution of magnetically-formed repelling forces ($F_R$) between medial and lateral aspects of the artificial knee, with benefits as previously described. Alternatively, or additionally, the mass, volume, thickness t, and/or overall magnetic field strength of the magnet 277 can be greater or less than the mass, volume, thickness t, and/or overall magnetic field strength of the magnet 279, thus allowing the potential of a complex magnetic field that provides an uneven distribution of magnetically-formed repelling forces ($F_R$) between medial and lateral aspects of the artificial knee, with benefits as previously described. The alternative embodiments described in relation to FIGS. 8 and 9 that do allow for an uneven distribution of magnetically-formed repelling forces ($F_R$) between medial and lateral aspects of the artificial knee can be incorporated based on analysis of the gait of the subject/patient or on the straightness or normality or lack of straightness or normality of the mid-ankle to mid-knee axis. Thus, a magnetically-formed corrective moment Mc (FIG. 7) can be applied by the magnetic total knee prosthesis 100. The magnetically-formed corrective moment Mc can aid the patient to feel more "normal" when walking. It can also serve to cause wear on the condyle surfaces 146, 148 and/or on the bearing surfaces 154, 156 to be about the same as each other, to increase the lifespan to the implant. Because the bearing surfaces 154, 156 are typically a lower hardness than the condyle surfaces 146, 148, minimizing their wear can also minimize the amount of particulate created, this also minimizing any related immune, inflammatory, or hypersensitive reactions by the subject's body.

Figure 10:
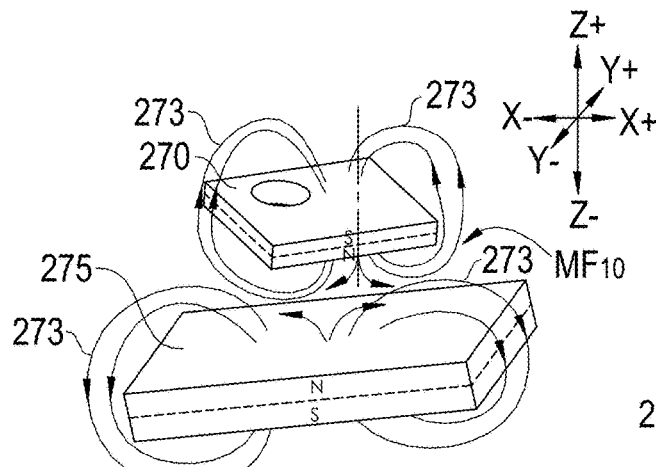
FIG. 10 is a perspective view of a first pole orientation of permanent magnets of a prosthesis, according to an embodiment of the present disclosure.
Figure 18:
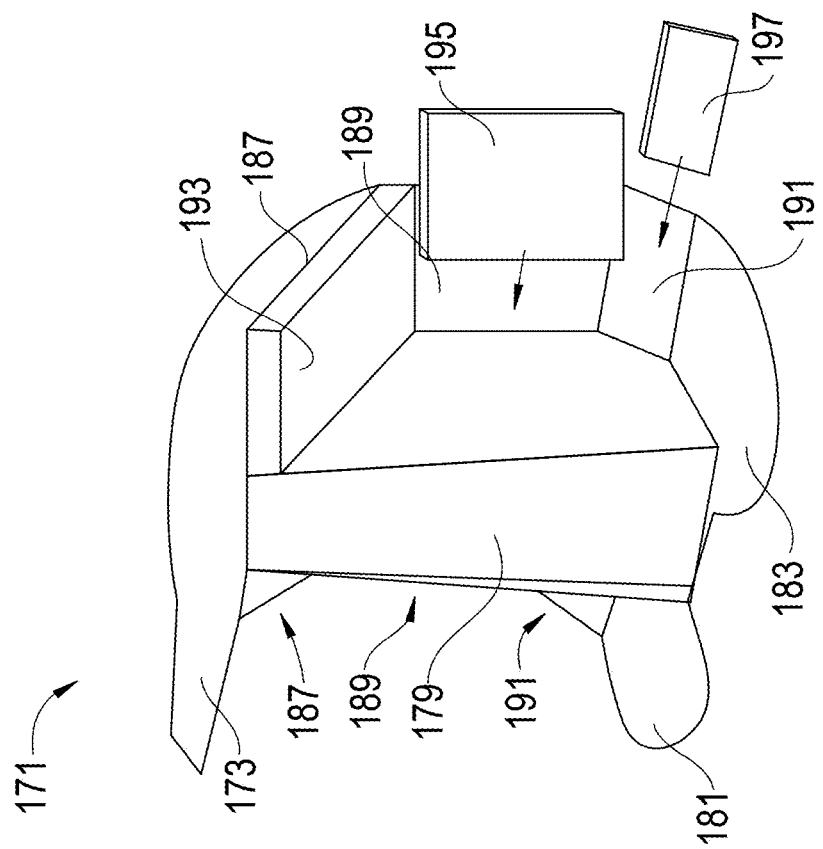
FIG. 18 is a partially-exploded rear perspective view of the magnetic total knee prosthesis of FIG. 17.
Figure 19:
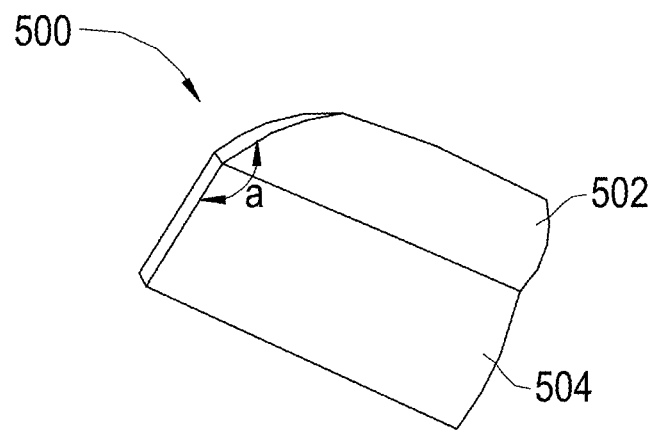
FIG. 19 is a perspective view of a magnet, according to an embodiment of the present disclosure.
Figure 20:
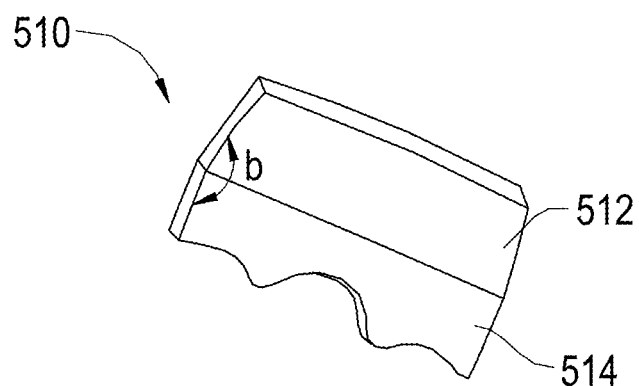
FIG. 20 is a perspective view of a magnet, according to an embodiment of the present disclosure.

In some embodiments, the opposing, repelling magnets need not be substantially parallel to each other in their neutral positions. For example, FIG. 10 illustrates a first permanent magnet 270 and a second permanent magnet 275 whose north poles N substantially face and oppose each other to create a repulsive magnetic field $MF_{10}$. The magnetic field $MF_{10}$ is represented by field lines 273. The first permanent magnet 270 is angulated from the second permanent magnet 275 along an x-axis, along a y-axis, and along a z-axis. However, the orientation of each of the first permanent magnet 270 and the second permanent magnet 275 still allows a significant amount of opposition between the two magnets 270, 275 (and their north poles), such that the resulting repulsive magnetic field $MF_{10}$ allows a significant magnetically-formed repelling force ($F_R$) (FIG. 6) when the magnetic total knee prosthesis 100 (or an alternative embodiment thereof) is implanted within and utilized by the patient 1. Thus, the permanent magnets used in the embodiments disclosed herein can be oriented in many different non-parallel manners. The non-parallelism may comprise offset or offsets from one, two, or three axes (X, Y, Z). Though generally flat and rectangular magnets are shown in FIGS. 1-16, 18, and 21-22, magnet shapes can be used that are more complex, and include varying thicknesses (FIGS. 19-20).

Figure 11:
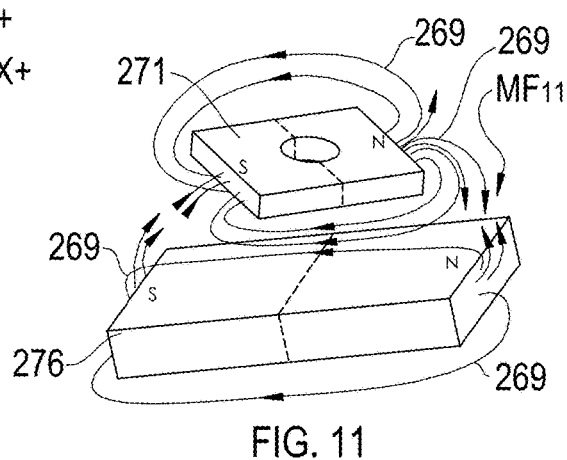
FIG. 11 is a perspective view of a second pole orientation of permanent magnets of a prosthesis, according to an embodiment of the present disclosure.

The magnets shown in FIGS. 1-10 are generally magnetized on an axis that passes through the thickness t of the magnetic material (see FIG. 8). However, FIG. 11 illustrates an alternative construction with magnetization along the longest axis (along the width W). A first permanent magnet 271 and a second permanent magnet 276 each have a north pole N and a south pole S. In their neutral orientation (e.g., with the femoral component in place over the tibial bearing and tibial component) the south pole S of the first permanent magnet 271 is substantially facing the south pole S of the second permanent magnet 276, and the north pole N of the first permanent magnet 271 is substantially facing the north pole N of the second permanent magnet 276. Thus, the like pole pairs each repel each other, resulting in the repulsive magnetic field $MF_{11}$ represented by field lines 269. The first permanent magnet 271 is angulated from the second permanent magnet 276 along an x-axis, along a y-axis, and along a z-axis, as are the magnets 270, 275 in FIG. 10. However, the orientation of each of the first permanent magnet 271 and the second permanent magnet 276 still allows a significant amount of opposition between the two magnets 271, 276 (and their respective north and south poles N, S), such that the resulting repulsive magnetic field allies a significant magnetically-formed repelling force ($F_R$) (FIG. 6) when the magnetic total knee prosthesis 100 (or an alternative embodiment thereof) is implanted within and utilized by the patient 1.

Figure 12:
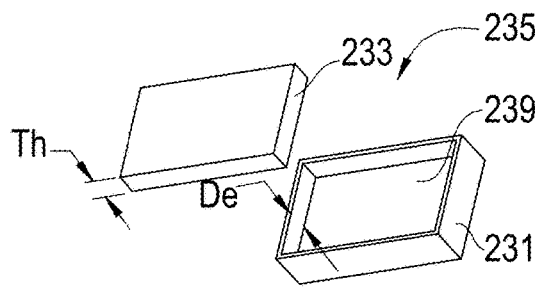
FIG. 12 is an exploded view of a magnetic assembly, according to an embodiment of the present disclosure.
Figure 13:
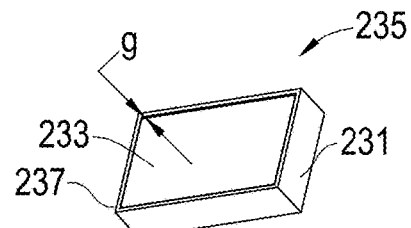
FIG. 13 is a perspective view of the magnetic assembly of FIG. 12.

Any of the permanent magnets described herein can comprise rare earth magnets, such as neodymium-iron-boron or samarium-cobalt magnets. In some embodiments, a layer of iron, or a layer of mu-metal (nickel-iron alloy) can be adhered or otherwise formed onto any of the magnets, in order to more drastically reshape the magnetic fields produced, and thus increase the overall repulsion. FIGS. 12-13 illustrate a configuration to protect the material of the magnets within the assemblies disclosed herein. A casing 231 and a permanent magnet 233 together form a magnetic assembly 235. The casing 231 comprises an interior space 239 having a depth De, and the magnet 233 has a thickness Th. The depth De is sufficiently greater than the thickness Th, such that when the magnet 233 is bonded into the casing 231, there is a recess gap g, wherein g=De−Th. The casing 231 can comprise a strong, durable non-magnetic metal, such as titanium, or can comprise a strong, durable ferrous material such as stainless steel or mu-metal. A non-magnetic material can be used when it is not desired to form any alternative shape to the magnetic field of the magnet 233, and a ferrous or otherwise magnetic material can be used when some about of additional shaping is desired. Because of the high-strength or high-hardness imparted by the material casing 231, and because of the protection of the magnet by the recess gap g, when the magnetic assembly 235 is secured to any load-bearing portions of a magnetic total knee prosthesis 100, the loads (forces, stresses, torsional, bending, compressive, or tensile) will all be placed primarily on the perimeter 237 of the casing 231 (in any direction), and not on the magnet 233. In some embodiments, the magnet 233 is bonded to the casing 231, within the interior 239 of the casing 231, with a flexible adhesive (e.g., urethane adhesive, silicone adhesive), such that deformation on the casing 231 does not in turn substantially deform the magnet 233. The protective nature of the casing 231 can be used in a more three-dimensional construction (e.g., tubular, bowl-shaped or hemispherical), and can even me utilized such that the majority of the tibial component 104 is constructed from magnetic material (e.g., neodymium-iron-boron) with a protective surrounding layer (400 series stainless-steel, 300 series stainless steel, iron, mu-metal). Thus, the entire tibial component 104 can be magnetized in some embodiments. This integral magnet configuration can also be used on the femoral component 102 in some embodiments.

Figure 14:
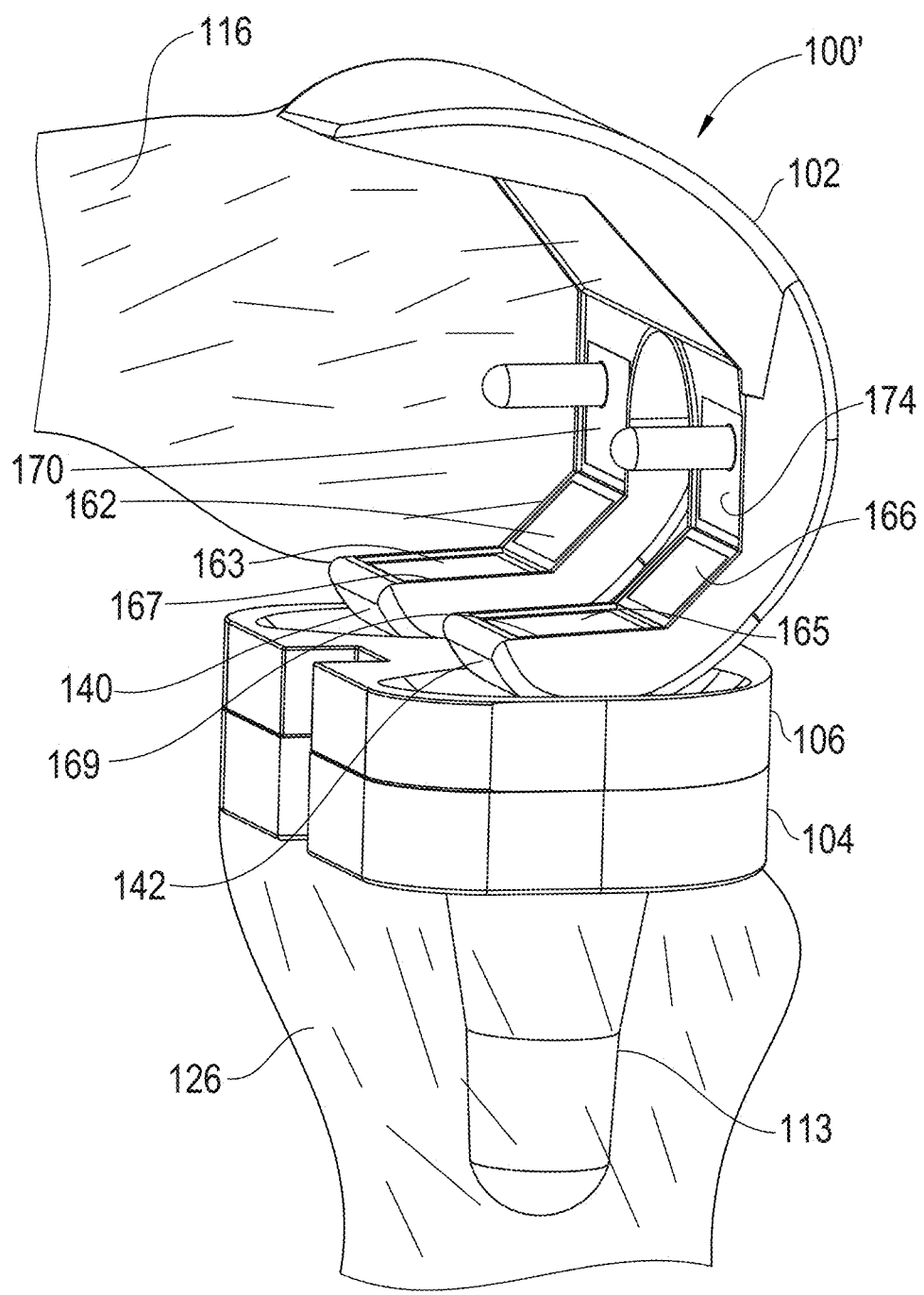
FIG. 14 is an alternative embodiment of a magnetic total knee prosthesis in a first position as implanted within a patient, according to an embodiment of the present disclosure.

FIG. 14 shows an alternative magnetic total knee prosthesis 100' having additional paired magnets 163, 165 secured within cavities 167, 169 (see also FIG. 3) at the end of the lateral condyle 140 and the medial condyle 142, respectively. In the generally 90° flexed position shown in FIG. 14, the additional pair of magnets 163, 165 can be effective, for example, when the magnetic total knee prosthesis 100' is implanted in in an active person or a person performing exercise or other activities that are more than simply walking and sitting. In some cases, there can be a combined effect from more than one pair of the condyle magnets. For example, in certain positions, the magnet pair 163, 165 and the magnet pair 162, 166 can substantially cooperate (work together) to repel the magnet 178, and in other positions, the magnet pair 162, 166 and the magnet pair 170, 174 can substantially cooperate (work together) to repel the magnet 178.

Returning to FIG. 2 and FIG. 4, the magnetic total knee prosthesis 100 can alternatively or additionally comprise one or more magnets that are configured to be secured to fourth face 138 and/or fifth face 139. Turning to FIG. 19, a magnet 500 includes a first section 502 and a second section 504. The first section 502 is angled from the second section 504 by an obtuse angle a. The first section 502 is configured to overlay some or all of the fifth face 139 and the second section 504 is configured to overlay some or all of the fourth face 138. Turning to FIG. 20, a magnet 510 includes a first section 512 and a second section 514. The first section 512 is angled from the second section 514 by an obtuse angle b. The first section 512 is configured to overlay some or all of the fourth face 138 and the second section 514 is configured to overlay an upper portion of the second faces 134a, 134b (FIG. 2). Thus, the magnet 500 of FIG. 19 and the magnet 510 of FIG. 20 each comprise monolithic magnets that are configured to cover more than one face of the femoral component 102. In some embodiments, the magnets 500, 510 can include curvilinear contours or three-dimensional surfaces. Thus, magnets can be configured to cover 1, 2, 3, 4, or 5 faces of the femoral component (paired together, or unpaired), or more if the femoral component has more than five faces (paired together or unpaired). The placement of a magnet on the fourth face 138 may aid in in creating a magnetically-formed "cushioning effect" as the femur/tibia are moved from flexion into extension. It can also aid in deceleration cushioning, while the subject descends stairs or a similar situation wherein stresses tend to cause hyperextension of the femur: running, jumping, pivoting, aggressively moving down a decline. Thus, function and stability of the knee joint is significantly enhanced. In alternative embodiments, a single magnet 170, 174 having a hole can be instead replaced by an upper magnet (above the peg 128, 130) and a lower magnet, thus not requiring holes in the magnets 170, 174. While offset holes are shown in the magnets 170, 174, alternatively, the holes can be centered, as can be the pegs 128, 130.

FIGS. 15 and 16 illustrate alternative manners of securing a magnet to the tibial side of the magnetic total knee prosthesis. The femoral components are not shown in FIG. 15 or 16, but can be similar to the femoral component 102 in the embodiment of FIGS. 1-7 or the embodiment of FIG. 14. In FIG. 15 a magnetic total knee prosthesis 300 includes a tibial component 304 a tibial bearing 306, and a magnet 378. As an alternative to the magnetic total knee prosthesis 100, the magnet 378 is configured to snap into a cavity 341 in the tibial component 304. Snaps 343, 345, 347 on the tibial component 304, around the cavity 341, are configured to allow the magnet 378 to be snapped into place. The tibial bearing 306 snaps into the tibial component 304 in a similar manner to the tibial bearing 106 and tibial component 104. Snaps 307, 308 in the tibial bearing 306 snap into tabs 309, 310 in the tibial component 304, respectively, at a front (anterior) side 311 of the prosthesis 300/tibial component 304. At a back (posterior) side 312 of the prosthesis 300/tibial component 304, the tibial component 304 includes a projection 313 which is configured to engage with a depression 314 in the back (posterior side) 312 of the tibial bearing 306. After the magnet 378 has been snapped in place within the tibial component 304, the projection 313 is first engaged with the depression 314, and then the snaps 307, 308 are engaged with the tabs 309, 310.

In FIG. 16 a magnetic total knee prosthesis 400 includes a tibial component 404 a tibial bearing 406, and a magnet 478. Combining features of both the magnetic total knee prosthesis 100 and the magnetic total knee prosthesis 300, the magnet 478 is configured to snap into a cavity 441 in the tibial component 404, and into a cavity 480 in the tibial bearing 406. Snaps 443, 445, 447 on the tibial component 404, around the cavity 441, are configured to allow the magnet 478 to be snapped into place in relation to the tibial component 404. The snaps 443, 445, 447 are configured to snap into undercuts 415, 416, 417 formed in the magnet 478, respectively. However, alternatively or additionally, the magnet 478 can also snap or bond to the tibial bearing 406. The tibial bearing 406 snaps into the tibial component 404 in a similar manner to the tibial bearing 306 and tibial component 304, using snaps 407, 408 and tabs 409, 410, and using the projection 413 and the depression 414.

Figure 17:
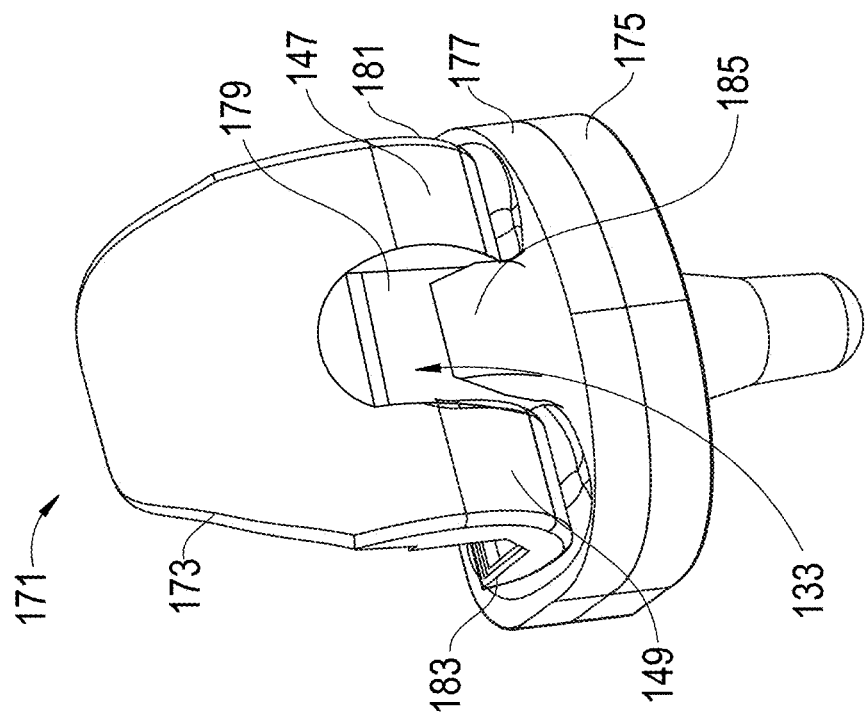
FIG. 17 is a front perspective view of a magnetic total knee prosthesis according to an embodiment of the present disclosure.
Figure 34:
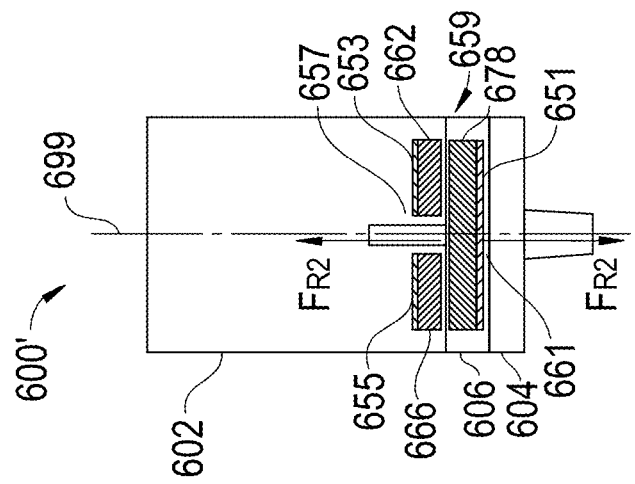
FIG. 34 is a front view of a magnetic total knee prosthesis, according to an embodiment of the present disclosure.

Alternative embodiments of the magnetic total knee prosthesis can comprise a "posterior stabilized" configuration, instead of a cruciate retaining configuration. FIGS. 17 and 18 illustrate a posterior stabilized magnetic total knee prosthesis 171, configured to be implanted within a patient 1 during a total knee arthroplasty surgery. The magnetic total knee prosthesis 171 comprises a femoral component 173, and tibial component 175, and a tibial bearing 177. The femoral component 173 comprises a box 179, shown from the anterior side in FIG. 17 and shown from the posterior side in FIG. 18. The box 179 is in the middle of the femoral component 173, between a first condyle 181 having a first curved condyle surface 147 and the second condyle 183 having a second curved condyle surface 149. The box 179 comprise a cavity 133 that is configured to engage with a post 185 which extends vertically on the tibial bearing 177. Thus, the engagement between the box 179 and the post 185 serves to control the total amount of angulation between the femoral component 173 and the tibial bearing 177/tibial component 175. The shape of the box 179 allows for three spaces 187, 189, 191 on each of the sides of the femoral component 173. A first permanent magnet 193 is configured to be secured into the first space 187. A second permanent magnet 195 is configured to be secured into the second space 189. A third permanent magnet 197 is configured to be secured into the first space 191. Identical or mirror-image magnets 193, 195, 197 can be secured to the spaces 187, 189, 191 on the opposite side. The magnet configurations/poles, etc. can comprise any of those disclosed herein. The magnets 193, 195, 197 need not have any holes, and can be clipped, screwed in, or secured with cement, adhesive, or epoxy. Mu metal or other ferrous plates can optionally be used to further shape the magnetic fields of one or more of the magnets 193, 195, 197 (as shown in FIG. 34). A larger magnetic field strength may be achievable with a magnet not having any holes. The number of total magnets on the femoral component 173 can comprise 1, 2, 3, 4, 5, 6, 7, or more. The number of total magnets on the tibial component 175 and/or on the tibial bearing 177 can comprise 1, 2, 3, 4, 5, 6, 7, or more. By being secured immediately adjacent the box 179, the magnets 193, 195, 197 are inherently stable and resistant to the effects of motion, such as slippage fracture or stresses. Stress risers that could damage the implant elements or damage the bone can be avoided.

Some surgeons may choose to implant a cruciate retaining design such as the magnetic total knee prosthesis 100, 100' for most or all patients, while others may choose the posterior stabilized design of magnetic total knee prosthesis 171 for most or all patients. Some surgeons may choose to implant a cruciate retaining design such as the magnetic total knee prosthesis 100, 100' for some patients, and the magnetic total knee prosthesis 171 for other patients. In some embodiments, an application ("app") for a mobile device (phone, tablet) or computer-program is provided to a user including at least one computer memory that is not a transitory signal, the at least one computer memory comprising instructions executable by at least one processor for determining the appropriate magnetic total knee prosthesis model. One or more of the following parameters are input: patient weight, level of bone deficiency, level of bone deformity, body mass index (BMI), width of femur or multiple transverse dimensions of femur, width of tibia or multiple transverse dimensions of tibia. The app or program executes to determine the appropriate model and/or size of the implant. In some embodiments, the app is configured to use input data to estimate the Wolff's forces, in order to minimize unwanted remodeling, or in some cases, even promote certain desirable remodeling or growth. In some embodiments, the implants can be modular, and the app can be configured to determine particular components of the prosthesis to combine. In some embodiments, the app can simply determine what thickness of a magnet to use, or what magnetic field strength of a magnet to use.

Because the embodiments described herein are configured to closely match current dimensions of total knee implants, the surgery to implant these magnetic total knee prostheses remains relatively the same.

Figure 21:
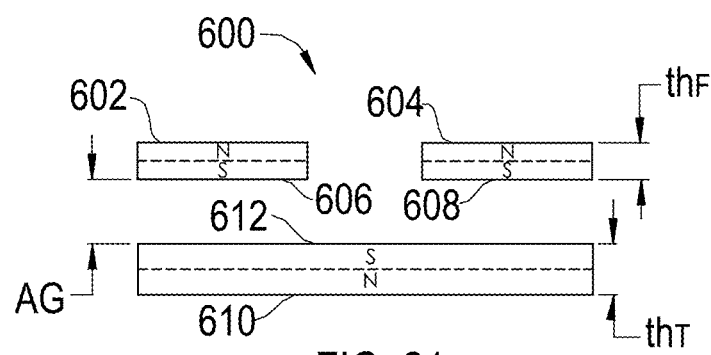
FIG. 21 is a side view of dimensions of a magnetic configuration, according to an embodiment of the present disclosure.

FIG. 21 illustrates thicknesses and separations ("air gaps," as they are often called, even if some of the gap does not constitute air or gas) between magnets in a generally representative magnetic configuration 600. The dimensions are representative, but are not limiting. First and second femoral magnets 602, 604 have lower faces 606, 608 and a tibial magnet 610 has an upper face 612. The south poles S of magnets 602, 604 each substantially face the south pole S od magnet 610 in this configuration, but alternatively, it could be the north poles N that face each other. The difference between the faces 606, 608 and the face 612 is termed an air gap AG, herein. Each of the femoral magnets 602, 604 has a thickness $th_F$ and the tibial magnet 610 has a thickness $th_T$. These values can each be considered average values, as in some embodiments, the magnets can have varying thickness and the configuration can be three-dimensional, and thus have a varying air gap AG. Thickness $th_F$ can be between about 0.075 inch (1.9 mm) and about 0.250 inch (6.35 mm), or between about 0.079 inch (2.0 mm) and about 0.197 inch (5.0 mm). Thickness $th_T$ cab be between about 0.125 inch (3.17 mm) and about 0.850 inch (21.6 mm), or between about 0.157 inch (4.0 mm) and about 0.787 inch (20.0 mm). Air gap AG can be between about 0.125 inch (3.17 mm) and about 1.5 inches (38.1 mm), or between about 0.20 inch (5.1 mm) and about 1.00 inch (25.4 mm), or between about 0.20 inch (5.1 mm) and about 0.50 inch (12.7 mm), or can be about 0.25 inch (6.35 mm). Turning to FIG. 3, the minimum vertical thickness of the tibial bearing 106 (e.g., at the bearing surfaces 154, 156) can be about 7 mm to about 20 mm, or about 8 mm to about 13 mm. This minimum vertical thickness extends from the face 199 of fifth cavity 180 (FIG. 4) to the extreme bottom 161 of the concave medial bearing surface 156. (Or, from the face 199 of fifth cavity 180 (FIG. 4) to the extreme bottom 159 of the concave lateral bearing surface 154.)

A single magnetically-formed repelling force ($F_R$) can be created by the magnets to be between about 0.1 pound (0.44 Newton) and about 30 pounds (133.4 Newtons) at a 0.25 air gap AG. Femoral magnets working together in repulsion against one or more tibial magnets can create a total magnetically-formed repelling force ($F_R$) of between about 0.2 pound (0.89 Newton) and about 60 pounds (266.9 Newton). In some embodiments a first magnetically-formed repelling force ($F_R$) of one femoral magnet/tibial magnet is about the same as a second magnetically-formed repelling force ($F_R$) of another femoral magnet/tibial magnet (one or more tibial magnet). In some embodiments a first magnetically-formed repelling force ($F_R$) of one femoral magnet/tibial magnet is greater than a second magnetically-formed repelling force ($F_R$) of another femoral magnet/tibial magnet (one or more tibial magnet). In some embodiments a first magnetically-formed repelling force ($F_R$) of one femoral magnet/tibial magnet is less than a second magnetically-formed repelling force ($F_R$) of another femoral magnet/tibial magnet (one or more tibial magnet).

FIG. 22 illustrates a magnetic total knee prosthesis 100" similar to the magnetic total knee prosthesis 100, however the tibial component 104", and a tibial bearing 106" are configured to screw together. One of more externally threaded portions 127, 129, 131 on the perimeter 117 of the tibial bearing 106" are configured to be threadingly engaged with one or more thin protrusion. In the magnetic total knee prosthesis 100" illustrated in FIG. 22, the engagement is in the counter-clockwise direction and disengagement is in the clockwise direction, but I alternative embodiments, the thread direction and the engagement/disengagement can be reversed.

FIG. 23 illustrates a magnetic total knee prosthesis 450 comprising a femoral component 452, a tibial component 454, and a tibial bearing 456. The tibial component 454 is similar to the tibial component 104 of FIGS. 1-7. The femoral component 452 and the tibial bearing 456 are otherwise similar to the femoral component 102 and tibial bearing 106, but are configured for placement of cylindrical permanent magnets. As shown in FIGS. 23 and 30, a lateral condyle 458 comprises a first transverse hole 462. A medial condyle 460 comprises a second transverse hole 464. The holes 462, 464 are cylindrical, although in alternative embodiments, the holes can have other shapes, such as a rectangular cross-section cut or groove or a square cross-section cut or groove. The placement of cylindrical holes in the femoral component 452 and the tibial bearing 456 simplifies the construction of the prosthesis 450. In some embodiments, the holes 462, 464 can each be machined into the condyle 458, 460 using a drill, reamer, or end mill. The machining can be manual or CNC. In other embodiments, the femoral component 452 can be formed having the holes 462, 464, for example by casting, electron beam melting, or metal additive manufacturing techniques such as material jetting, material extrusion, powder bed fusion, binder jetting, or directed energy deposition. The holes 462, 464 are configured for the placement of cylindrical permanent magnets 466. Magnet 466 is illustrated in FIGS. 24-25 and is poled radially, having south S and north N poles. The magnet 466 can comprise any of the materials described in relation to the other permanent magnets disclosed herein. The magnets 466 can be secured within holes 462, 464 using adhesive, hot melt, or epoxy. Any of the magnets described herein in relation to any of the embodiments can have a plating or a sputtered protective coating, such as nickel, zinc, or gold. In some embodiments, as shown in FIG. 30, the location of the center of the hole 462, the diameter of the magnet 466 (and diameter of the hole 462), and the rotational orientation of the magnet 466 can be controlled such that the desired close pole (south S, in FIG. 30) can be located close (distance a) in one orientation of the femoral component 452, and also located close (distance b) in another orientation of the femoral component 452. Furthermore, the south S pole is located close (distance c) in an orientation between these two orientations.

The top of the tibial bearing 456 is illustrated in FIG. 28 and the bottom of the tibial bearing 456 is illustrated in FIG. 29. Holes 468, 470 are placed in the tibial bearing 456, entering from a bottom surface 472. In some embodiments, the holes 468, 470 can each be machined into the tibial bearing 456 using a drill, reamer, or end mill. The machining can be manual or CNC. In other embodiments, the tibial bearing 456 can be formed having the holes 468, 470, for example by casting, electron beam melting, additive manufacturing techniques such as fused filament fabrication, multi-jet fusion, selective laser sintering, stereolithography, and digital light processing, or subtractive manufacturing techniques such as laser jet cutting or water jet cutting. The holes 468, 470 are configured for the placement of cylindrical permanent magnets 474. Magnet 474 is illustrated in FIGS. 26-27 and is poled axially, having south S and north N poles. The magnet 474 can comprise any of the materials described in relation to the other permanent magnets disclosed herein. The magnets 474 can be secured within holes 468, 470 using adhesive, hot melt, or epoxy. Any of the magnets described herein in relation to any of the embodiments can have a plating or a sputtered protective coating, such as nickel, zinc, or gold.

The magnetic total knee prosthesis 450 of FIGS. 23-30 is shown in a generally symmetric configuration such that it can be used on either a left knee or a right knee, thus, the terms "medial" and "lateral" can be interchanged in other embodiments. Furthermore, certain adjustments or retrofits are possible to further modify the magnetic total knee prosthesis 450 to be used on a right knee or a left knee. Though a south S to south S repulsive arrangement is shown in the prosthesis 450, alternatively, the magnets can all be reversed such that it is a north N to north N repulsive arrangement.

Turning to FIG. 23, in some embodiments, the effective height h of the base 476 of the tibial bearing 456 can range from about 5 mm to about 25 mm, or about 10 mm to about 15 mm. The diameter of the holes 468, 470 can be substantially the same or slightly larger than the diameter D of the magnet 474, and can range from about 0.25 inch (6.35 mm) to about 1.0 inch (25.4 mm), or between about 0.35 inch (8.89 mm) and about 0.65 inch (16.5 mm). The depth of the holes 468, 470 can be substantially the same or slightly longer than the length L of the magnet 474, and can range from about 2 mm to about 18 mm, or about 3 mm to about 8 mm (FIG. 26). The diameter d of the magnet 466 can range from about 2 mm to about 15 mm, or about 5 mm to 10 mm. The intermagnetic distance IMD can range from about 0.125 inch (3.17 mm) to about 0.8 inch (20.3 mm), or between about 0.25 inch (6.35 mm) and about 0.65 inch (16.5 mm), or about 0.315 inch (8 mm) to about 0.472 inch (12 mm). Typically, the lower magnetic distance thL (in the tibial bearing 456) is about 6 mm to about 10 mm, or about 7 mm to about 9 mm, or about 8 mm. And typically, the upper magnetic distance thU (in the condyle 458, 460) is about 3 mm to about 5 mm, or about 4 mm. Thus, the intermagnetic distance IMD is typically about 10 mm to about 14 mm, or about 12 mm. Improvements in materials technology (strength, durability) will allow these numbers to be further reduced. In any of the embodiments disclosed herein, permanent neodymium-iron-boron magnets can comprise a grade ranging between N42 and N52.

In some alternative embodiments, the femoral component 102 with any of magnets 162, 166, 170, 174 (or the alternative magnets) can be used in a magnetic total knee prosthesis with the tibial bearing 456 having magnets 474. FIG. 42 illustrates another alternative embodiment in this same spirit. In some other alternative embodiments, the femoral component 452 having magnets 466 can be used in a magnetic total knee prosthesis with the tibial bearing 106 having magnet 178. The holes 462, 464, 468, 470 serve to protect the magnets 466, 474, but also serve to protect the magnetic total knee prosthesis 450 from degradation cause by biological growth (e.g., bone, soft tissue, protein deposits, etc.) or by repetitive use of the knee. The holes 462, 464, 468, 470 also serve to protect the tissue and overall systems (lymphatic, vascular, nervous, muscular, etc.) from the material of the magnets 466, 474 (as would any magnetic protective coating).

Figure 32:
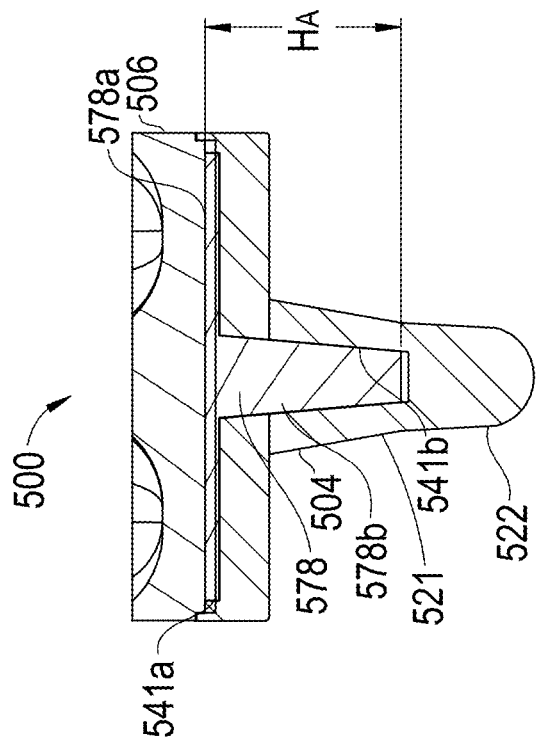
FIG. 32 is a cross-sectional view of the tibial portion of the magnetic total prosthesis of FIG. 31.
Figure 31:
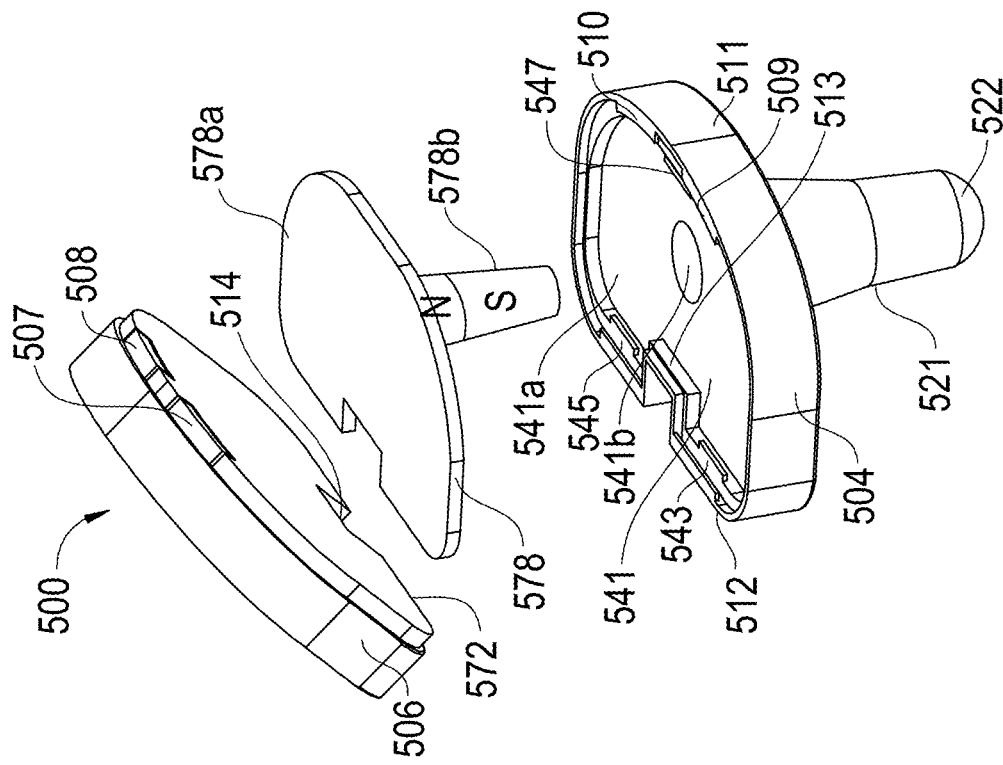
FIG. 31 is an exploded view of an alternative embodiment of a tibial portion of a magnetic total knee prosthesis, according to an embodiment of the present disclosure.

FIGS. 31 and 32 illustrate an alternative tibial side of the magnetic total knee prosthesis 500. The femoral components are not shown, but can be similar to the femoral component 102 in the embodiment of FIGS. 1-7 or the embodiment of FIG. 14, or the embodiment of FIG. 23, or combinations thereof. In FIGS. 21-32 the magnetic total knee prosthesis 500 includes a tibial component 504 a tibial bearing 506, and a magnet 578. The magnet 578 is configured to snap into a cavity 541 in the tibial component 504. The cavity 541 comprises a substantially planar upper cavity portion 541*a*, and an elongate vertical lower cavity portion 541*b*, integral with extending downwardly from the upper cavity portion 541*b*. The magnet 578 comprises a substantially planar upper magnet portion 578*a* and an elongate vertical lower magnet portion 578*b*, integral with and extending downwardly from the upper magnet portion 578*a*. The magnet 578 can be machined or otherwise configured in its shape as a monolithic object, and then subsequently magnetized, as shown (south pole S, north pole N). Opposite poling is another possible alternative embodiment, as appropriate to create the desired effect vs. the femoral component (e.g., repelling/repulsive). Snaps 543, 545, 547 on the tibial component 504, around the upper cavity portion 541*a*, are configured to allow the upper portion 578*a* of the magnet 578 to be snapped into place, to thus hold the magnet 578 in place. The tibial bearing 506 snaps into the tibial component 504 in a similar manner to the tibial bearing 106 and tibial component 104. Snaps 507, 508 in the tibial bearing 506 snap into tabs 509, 510 in the tibial component 504, respectively, at a front (anterior) side 511 of the prosthesis 500/ tibial component 504. At a back (posterior) side 512 of the prosthesis 500/tibial component 504, the tibial component 504 includes a projection 513 which is configured to engage with a depression 514 in the back (posterior side) 512 of the tibial bearing 506. After the magnet 578 has been inserted in the cavity 541, it can be snapped in place within the tibial component 504, and then the projection 513 is first engaged with the depression 514, and then the snaps 507, 508 are engaged with the tabs 509, 510.

As visible in FIG. 32, the lower portion 578*b* of the magnet 578 is thus tucked within the stem 521 of the tibial coupler 522. The lower cavity portion 514*b* makes space for the lower magnet portion 578*b*, and thus allows the magnet 578 to have a significantly increased axial height HA, and increased mass and volume. Thus, the magnet 578 can have a significantly larger magnetic field strength to provide (with the magnet(s) associated with the femoral component) a significantly larger repulsive force, to more significantly counteract normal forces on the knee joint.

Figure 33:
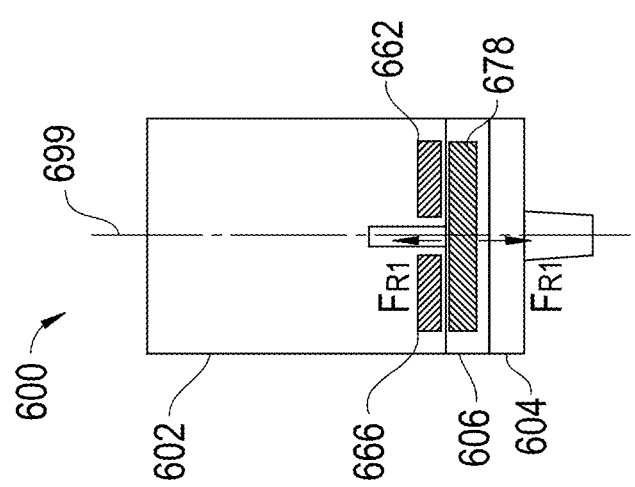
FIG. 33 is a front view of a magnetic total knee prosthesis, according to an embodiment of the present disclosure.

FIG. 33 illustrates a generic magnetic total knee prosthesis 600 which is intended to generally represent a femoral component 602, a tibial component 604 and a tibial bearing 606. The femoral component 602 has two magnets 662, 666 and the tibial bearing 606 (and/or tibial component) has a magnet 678 configured to repel each of the magnets 662, 666. Any of the magnetic total knee prosthesis embodiments described herein can alternatively be made in the manner of the magnetic total knee prosthesis 600' shown in FIG. 34, utilizing magnetic shielding on one or more of its magnets. The magnetic total knee prosthesis 600' is similar to the magnetic total knee prosthesis 600, except that it further comprises: a first ferrous magnetic shield 653 substantially covering and substantially adjacent to the magnet 662 on the upper side 657 of the magnetic assembly 659; a second ferrous magnetic shield 655 substantially covering and substantially adjacent to the magnet 666 on the upper side 657 of the magnetic assembly 659; and a third magnetic shield 651 substantially covering and substantially adjacent to the magnet 678 on the lower side 661 of the magnetic assembly 659. In some embodiments, the shields 651, 653, 655 comprise a nickel-iron alloy. In some embodiments, the shields 651, 653, 655 comprise a mu-metal. The shields 651, 653, 655 can include 49% to 85% nickel. In some embodiments, the alloy also includes small amounts (1% to 8% of silicon or 1% to 8% of molybdenum). The effect of the shields 651, 653, 655 is to shape the magnetic fields toward the longitudinal axis 699 and to thus increase the magnetically-formed repelling force ($F_R$). The magnetically-formed repelling force $F_{R2}$ in the magnetic total knee prosthesis 600' of FIG. 34 is significantly larger than the magnetically-formed repelling force $F_{R1}$ in the magnetic total knee prosthesis 600 of FIG. 33, as can be seen from the proportional vector lengths (indicating magnitude) in FIGS. 33 and 34.

Figure 35:
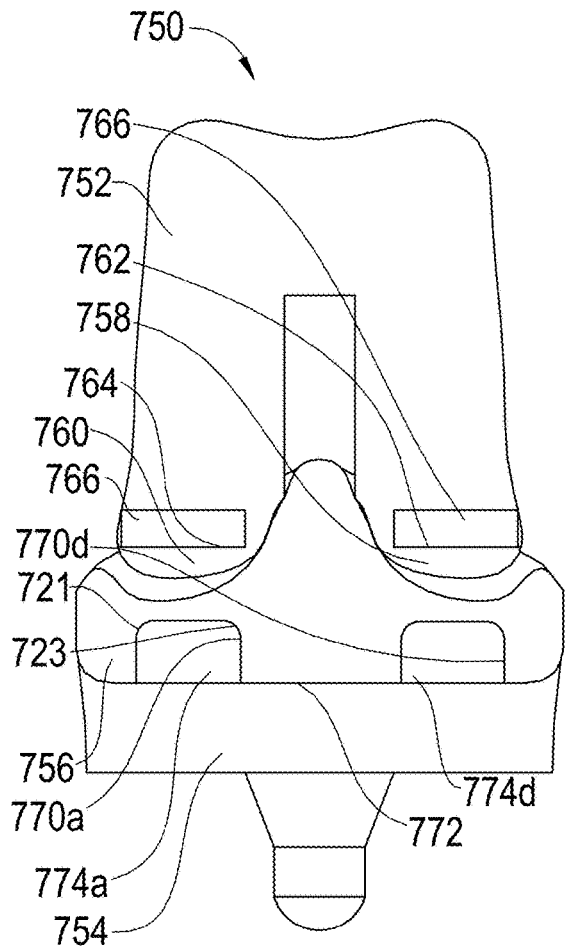
FIG. 35 is a front view of a magnetic total knee prosthesis, according to an alternative embodiment of the present disclosure.
Figure 36:
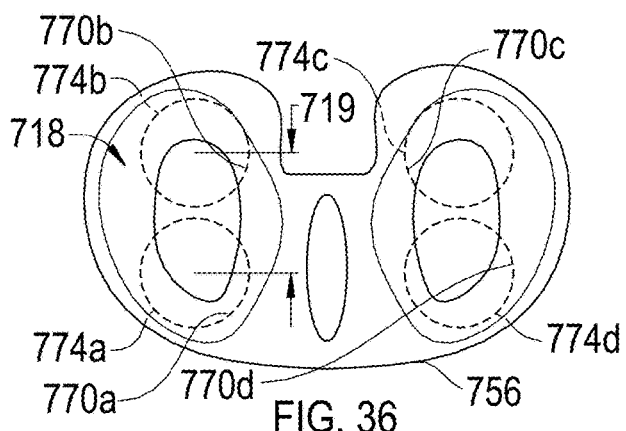
FIG. 36 is a top view of the tibial bearing of FIG. 35.

FIG. 35 illustrates a magnetic total knee prosthesis 750 comprising a femoral component 752, a tibial component 754, and a tibial bearing 756. The tibial component 754 is similar to the tibial component 454 of FIG. 23. The femoral component 752 is similar to the femoral component 452 of FIG. 23, though alternatively can be similar to the tibial bearing 102 of FIG. 1. As shown in FIGS. 35 and 36, a lateral condyle 758 comprises a first transverse hole 762. A medial condyle 760 comprises a second transverse hole 764. The holes 762, 764 are cylindrical, although in alternative embodiments, the holes can have other shapes, such as a rectangular cross-section cut or groove or a square cross-section cut or groove. The placement of cylindrical holes in the femoral component 752 simplifies the construction of the prosthesis 750. In some embodiments, the holes 762, 764 can each be machined into the condyle 758, 760 using a drill, reamer, or end mill. The machining can be manual or CNC. In other embodiments, the femoral component 752 can be formed having the holes 762, 764, for example by casting, electron beam melting, or metal additive manufacturing techniques such as material jetting, material extrusion, powder bed fusion, binder jetting, or directed energy deposition. The holes 762, 764 are configured for the placement of cylindrical permanent magnets 766. Magnet 766 can be similar to the magnet 466 in FIGS. 24-25. The magnet 766 can comprise any of the materials described in relation to the other permanent magnets disclosed herein. The magnets 766 can be secured within holes 762, 764 using adhesive, hot melt, or epoxy. Any of the magnets described herein in relation to any of the embodiments can have a plating or a sputtered protective coating, such as nickel, zinc, or gold.

The top of the tibial bearing 756 is illustrated in FIG. 36. Holes 770 (770*a-d*) are placed in the tibial bearing 756, entering from a bottom surface 772. In some embodiments, the holes 770 (770*a-d*) can each be machined into the tibial bearing 756 using a drill, reamer, or end mill. The machining can be manual or CNC. In other embodiments, the tibial bearing 756 can be formed having the holes 770 (770*a-d*), for example by casting, electron beam melting, additive manufacturing techniques such as fused filament fabrication, multi-jet fusion, selective laser sintering, stereolithography, and digital light processing, or subtractive manufacturing techniques such as laser jet cutting or water jet cutting. The holes 770 (770*a-d*) are configured for the placement of four cylindrical permanent magnets 774 (774*a-d*). Magnets 774 are each poled axially, similar to the magnet 474 of FIGS. 26-27. The magnets 774 can comprise any of the materials described in relation to the other permanent magnets disclosed herein. The magnets 774 can be secured within holes 770 using adhesive, hot melt, or epoxy. Any of the magnets described herein in relation to any of the embodiments can have a plating or a sputtered protective coating, such as nickel, zinc, or gold. The placement and orientation of the array 718 of magnets 774*a-d* (magnet 774*a* into hole 770*a*, magnet 774*b* into hole 770*b*, etc.) further facilitates the south S-to-south S repelling configuration (between magnets 774 and magnet 766), regardless of the rotational position/orientation of the femoral component 752. For example, referring to FIG. 30, when dimension b is the facing dimension (as shown), or whether dimension c is the facing dimension, or whether dimension a is the facing dimension. Having two magnets (e.g., 774*a*, 774*b*) with south poles S superiorly-facing (up), as in FIG. 26, and spread anteriorly-posteriorly (dimension 719) ensures good repulsion vs. south pole S of magnet 766 (see orientation of magnet 466 of FIG. 30 as an example). In an alternative embodiment, instead of magnets 744*a-d* being poled axially, they can each be poled radially (north N on one side/semi-cylinder, south S on the other side/semi-cylinder). Furthermore, they can all have their north N poles oriented outwardly and their south S poles oriented inwardly, the south S poles thus facing the south S pole of magnet 766 as the femoral component 752 rotates. Each magnet 774 includes a circumferentially surrounding fillet 721. Each hole 770 includes an internal fillet 723 having a contour that matches the contour of the fillet 721 of the magnet 774. The fillets 723 eliminate a stress riser that would occur from a non-fileted end of the hole 770. Thus, durability is added to the femoral bearing 756.

Figure 37:
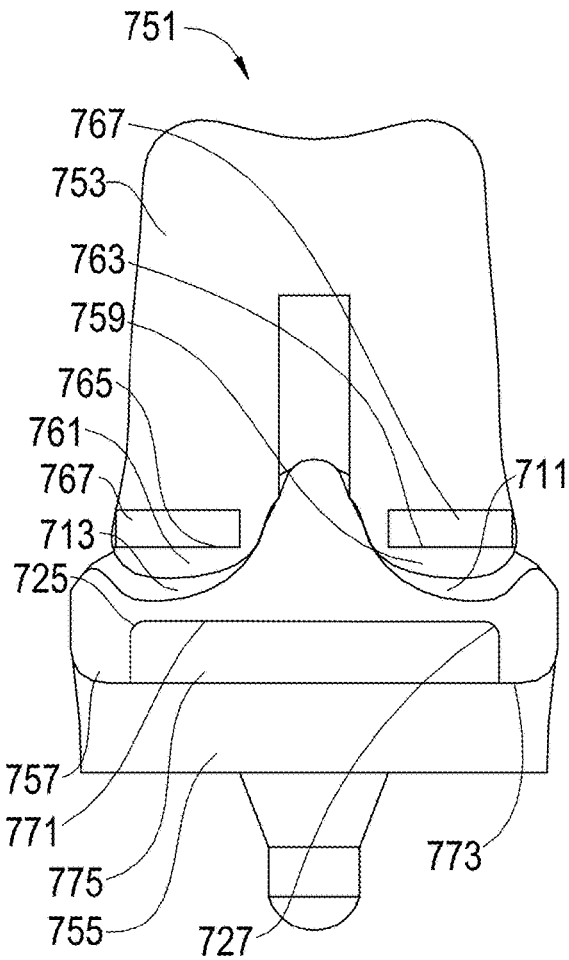
FIG. 37 is a front view of a magnetic total knee prosthesis, according to an alternative embodiment of the present disclosure.
Figure 38:
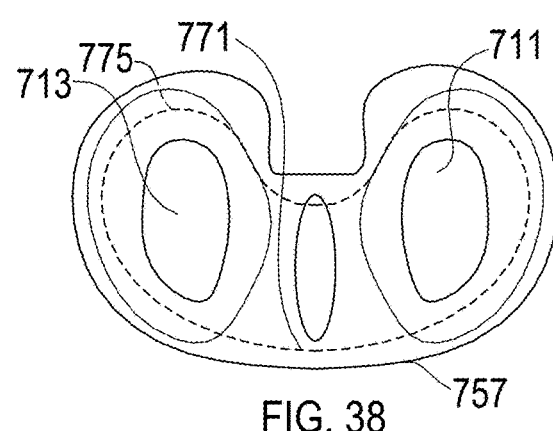
FIG. 38 is a top view of the tibial bearing of FIG. 37.

FIG. 37 illustrates a magnetic total knee prosthesis 751 comprising a femoral component 753, a tibial component 755, and a tibial bearing 757. The tibial component 755 is similar to the tibial component 454 of FIG. 23. The femoral component 753 is similar to the femoral component 452 of FIG. 23, though alternatively can be similar to the tibial bearing 102 of FIG. 1. As shown in FIGS. 37 and 38, a lateral condyle 759 comprises a first transverse hole 763. A medial condyle 761 comprises a second transverse hole 765. The holes 763, 765 are cylindrical, although in alternative embodiments, the holes can have other shapes, such as a rectangular cross-section cut or groove or a square cross-section cut or groove. The placement of cylindrical holes in the femoral component 753 simplifies the construction of the prosthesis 751. In some embodiments, the holes 763, 765 can each be machined into the condyle 759, 761 using a drill, reamer, or end mill. The machining can be manual or CNC.

In other embodiments, the femoral component 753 can be formed having the holes 763, 765, for example by casting, electron beam melting, or metal additive manufacturing techniques such as material jetting, material extrusion, powder bed fusion, binder jetting, or directed energy deposition. The holes 763, 765 are configured for the placement of cylindrical permanent magnets 767. Magnet 767 can be similar to the magnet 466 in FIGS. 24-25. The magnet 767 can comprise any of the materials described in relation to the other permanent magnets disclosed herein. The magnets 767 can be secured within holes 763, 765 using adhesive, hot melt, or epoxy. Any of the magnets described herein in relation to any of the embodiments can have a plating or a sputtered protective coating, such as nickel, zinc, or gold.

The top of the tibial bearing 757 is illustrated in FIG. 38. Hole 771 is placed in the tibial bearing 757, entering from a bottom surface 773. In some embodiments, the hole 771 can be machined into the tibial bearing 757 using a drill, reamer, or end mill. The machining can be manual or CNC. In other embodiments, the tibial bearing 757 can be formed having the hole 771, for example by casting, electron beam melting, additive manufacturing techniques such as fused filament fabrication, multi-jet fusion, selective laser sintering, stereolithography, and digital light processing, or subtractive manufacturing techniques such as laser jet cutting or water jet cutting. The hole 771 is configured for the placement of a permanent magnet 775. Magnets 775 is poled axially, similar to the magnet 474 of FIGS. 26-27. The magnet 775 can comprise any of the materials described in relation to the other permanent magnets disclosed herein. The magnet 775 can be secured within hole 771 using adhesive, hot melt, or epoxy. Any of the magnets described herein in relation to any of the embodiments can have a plating or a sputtered protective coating, such as nickel, zinc, or gold. The placement and orientation of the magnet 775 (into hole 771) further facilitates the south S-to-south S repelling configuration, regardless of the rotational position/orientation of the femoral component 752, because the kidney-shaped magnet 775 (or bean-shaped, or alternatively, horseshoe-shaped) is well placed in relation to the concave lateral bearing surface 711 and the concave medial bearing surface 713 in which the lateral condyle 759 and the lateral condyle 761 slide and translate, respectively. The magnet 775 includes a circumferentially surrounding fillet 725. Each hole 771 includes an internal fillet 727 having a contour that matches the contour of the fillet 725 of the magnet 775. The fillets 727 eliminate a stress riser that would occur from a non-fileted end of the hole 771. Thus, durability is added to the femoral bearing 757.

FIG. 39 illustrates a magnetic total knee prosthesis 850 comprising a femoral component 852, a tibial component 854, and a tibial bearing 856. The tibial component 854 is similar to the tibial component 454 of FIG. 23. The femoral component 852 is similar to the femoral component 452 of FIG. 23, though alternatively can be similar to the tibial bearing 102 of FIG. 1. As shown in FIG. 39, a lateral condyle 858 comprises a first transverse hole 862. A medial condyle 860 comprises a second transverse hole 864. The holes 862, 864 are cylindrical, although in alternative embodiments, the holes can have other shapes, such as a rectangular cross-section cut or groove or a square cross-section cut or groove. The placement of cylindrical holes in the femoral component 852 simplifies the construction of the prosthesis 850. In some embodiments, the holes 862, 864 can each be machined into the condyle 858, 860 using a drill, reamer, or end mill. The machining can be manual or CNC. In other embodiments, the femoral component 852 can be formed having the holes 862, 864, for example by casting, electron beam melting, or metal additive manufacturing techniques such as material jetting, material extrusion, powder bed fusion, binder jetting, or directed energy deposition. The holes 862, 864 are configured for the placement of cylindrical permanent magnets 866. Magnet 866 can be similar to the magnet 466 in FIGS. 24-25. The magnet 866 can comprise any of the materials described in relation to the other permanent magnets disclosed herein. The magnets 866 can be secured within holes 862, 64 using adhesive, hot melt, or epoxy. Any of the magnets described herein in relation to any of the embodiments can have a plating or a sputtered protective coating, such as nickel, zinc, or gold.

The tibial bearing 856 includes holes 868, 870 entering from a bottom surface 872. In some embodiments, the holes 868, 870 can each be machined into the tibial bearing 856 using a drill, reamer, or end mill. The machining can be manual or CNC. In other embodiments, the tibial bearing 856 can be formed having the holes 868, 870, for example by casting, electron beam melting, additive manufacturing techniques such as fused filament fabrication, multi jet fusion, selective laser sintering, stereolithography, and digital light processing, or subtractive manufacturing techniques such as laser jet cutting or water jet cutting. The holes 868, 870 are configured for the placement of cylindrical permanent magnets 874. Magnets 874 are each poled axially, similar to the magnet 474 of FIGS. 26-27. The magnets 874 can comprise any of the materials described in relation to the other permanent magnets disclosed herein. The magnets 874 can be secured within holes 868, 870 using adhesive, hot melt, or epoxy. Any of the magnets described herein in relation to any of the embodiments can have a plating or a sputtered protective coating, such as nickel, zinc, or gold. Each magnet 874 includes a circumferentially surrounding fillet 821 (FIGS. 39-40). Each hole 870 includes an internal fillet 823 having a contour that matches the contour of the fillet 821 of the magnet 874. The fillets 823 eliminate a stress riser that would occur from a non-fileted end of the hole 870. Thus, durability is added to the femoral bearing 856. Furthermore, each magnet 874 includes a concave bowl-shaped center top portion 827. Each hole 870 include can optionally include a matching convex portion 829, though this is optional. The top portion 827 of the magnet 874 (and the convex portion 829) can be tailored by depth, radius and diameter, such that a consistent thickness between the top contour 831 of the magnet 874 and the concave lateral bearing surface 815 (or the concave medial bearing surface 817) occurs throughout the proximity of the magnet 874. Thus, the stress levels within the material of the tibial bearing 856 are controlled, and failure modes are diminished, further increasing durability. In other embodiments, if a stress analysis is done, and non-equal, varying thicknesses between the top contour 831 of the magnet 874 and the concave lateral bearing surface 815 (or the concave medial bearing surface 817) are the solution of reducing stresses in the tibial bearing 856, then the top contour 831/center top portion 827 and/or the convex portion 829 can be modified as needed to lower overall stresses or lower maximum stresses.

FIG. 41 illustrates a tibial bearing 882 of a magnetic total knee prosthesis 880 that is similar to the tibial bearing 456 of FIGS. 23 and 28-29, however the tibial bearing 882 includes two elliptically-shaped magnets 881, 883. The major axis 884 and minor axis 885 of the magnets 881, 883 are chosen so that the magnets 881, 883 share a similar shape and an appropriate size in relation to the concave lateral bearing surface 886 or the concave medial bearing surface 887. The magnets 881, 883 can each be poled axially (as described in relation to the magnet 474 of FIG. 26) or can each be poled laterally (as shown in the alternative marking in magnet 881). In this alternative embodiment, magnet 883 can be configured as a mirror image of magnet 881.

FIGS. 42-43 illustrate a magnetic total knee prosthesis 950 comprising a femoral component 952, a tibial component 954, and a tibial bearing 956. The tibial component 954 is similar to the tibial component 854 of FIG. 39. The femoral component 952 is similar to the femoral component 102 of FIG. 1. The tibial bearing 956 is similar to the tibial bearing 856 of FIGS. 39 and 41, except that the magnets 981, 983, instead of having an elliptical shape, have a shape substantially the same as the concave lateral bearing surface 986 or the concave medial bearing surface 987. The magnets 981, 983 are each fully three-dimensionally contoured. The magnets 981, 983 each have an upper contour (see upper contour 999 of magnet 981 in FIG. 42) that three-dimensionally matches the concave lateral bearing surface 986 or the concave medial bearing surface 987. Thus, the stress levels within the material of the tibial bearing 956 are controlled, and failure modes are diminished, further increasing durability. In other embodiments, if a stress analysis is done, and non-equal, varying thicknesses between the upper contour 999 of the magnet 981 (or magnet 083) and the concave lateral bearing surface 986 (or the concave medial bearing surface 987) are the solution of reducing stresses in the tibial bearing 956, then the upper contour 999 and/or the concave lateral bearing surface 986 can be modified as needed to lower overall stresses or lower maximum stresses.

The following clauses include examples of apparatus of the disclosure.

Clause 1: In one example, an orthopedic knee prosthesis includes a femoral component having a top portion and a bottom portion, the femoral component including a femoral coupler configured to couple to a lower portion of a femur, the bottom portion including a curved medial condyle surface and a curved lateral condyle surface, a tibial bearing having a top portion including: a concave medial bearing surface configured to articulate with the curved medial condyle surface, and a concave lateral bearing surface configured to articulate with the curved lateral condyle surface, a tibial component having a bottom portion and a top portion, the bottom portion including a tibial coupler configured to couple to an upper portion of a tibia, the top portion including a tibial bearing coupler configured to couple to the tibial bearing, a first magnetic portion associated with the femoral component and configured to be in proximity to at least a portion of the of the curved medial condyle surface, the first magnetic portion having a first pole and a second pole, the second pole having the opposite polarity of the first pole, a second magnetic portion associated with the femoral component and configured to be in proximity to at least a portion of the of the curved lateral condyle surface, the second magnetic portion having a third pole and a fourth pole, the fourth pole having the opposite polarity of the third pole, a third magnetic portion associated with one or both of the tibial bearing and/or the tibial component and configured to be in proximity to at least a portion of the concave medial bearing surface, the third magnetic portion having a fifth pole and a sixth pole, the sixth pole having the opposite polarity of the fifth pole, and a fourth magnetic portion associated with one or both of the tibial bearing and/or the tibial component and configured to be in proximity to at least a portion of the concave lateral bearing surface, the fourth magnetic portion having a seventh pole and an eighth pole, the eighth pole having the opposite polarity of the seventh pole, and wherein when (a) the tibial bearing is coupled to the tibial component, (b) the concave medial bearing surface articulates with the curved medial condyle surface, and (c) the concave lateral bearing surface articulates with the curved lateral condyle surface: the fifth pole is configured to substantially oppose the first pole in sufficient proximity to thereby produce a first repulsive force and the seventh pole is configured to substantially oppose the third pole in sufficient proximity to thereby produce a second repulsive force.

Clause 2: In some examples, the prosthesis includes clause 1, wherein the first repulsive force is between about 0.1 pounds and about 30 pounds at a distance between the first pole and the fifth pole of about 0.25 inch.

Clause 3: In some examples, the prosthesis includes either one of clauses 1 or 2, wherein the second repulsive force is between about 0.1 pound and about 30 pounds at a distance between the third pole and the seventh pole of about 0.25 inch.

Clause 4: In some examples, the prosthesis includes any one of clauses 1-3, wherein the combination of the first repulsive force and the second repulsive force results in a distraction force between the tibia and the femur of between about 0.2 pound and about 60 pounds at a distance between the third pole and the seventh pole of about 0.25 inch.

Clause 5: In some examples, the prosthesis includes any one of clauses 1-4, wherein the first repulsive force is about the same as the second repulsive force.

Clause 6: In some examples, the prosthesis includes any one of clauses 1-4, wherein the first repulsive force is greater than the second repulsive force.

Clause 7: In some examples, the prosthesis includes any one of clauses 1-4, wherein the first repulsive force is less than the second repulsive force.

Clause 8: In some examples, the prosthesis includes any one of clauses 1-7, wherein the first magnetic portion is integral to the femoral component.

Clause 9: In some examples, the prosthesis includes any one of clauses 1-7, wherein the second magnetic portion is integral to the femoral component.

Clause 10: In some examples, the prosthesis includes clause 9, wherein the first magnetic portion is integral to the femoral component.

Clause 11: In some examples, the prosthesis includes any one of clauses 1-7, wherein the second magnetic portion includes a magnet.

Clause 12: In some examples, the prosthesis includes any one of clauses 1-7, wherein the first magnetic portion includes a first magnet.

Clause 13: In some examples, the prosthesis includes clause 12, wherein the second magnetic portion includes a second magnet.

Clause 14: In some examples, the prosthesis includes either one of clauses 12 or 13, wherein the first magnet includes a magnetic shim.

Clause 15: In some examples, the prosthesis includes either one of clauses 12 or 13, wherein the first magnet includes a rare earth magnet.

Clause 16: In some examples, the prosthesis includes clause 12, wherein the first magnet includes neodymium-iron-boron.

Clause 17: In some examples, the prosthesis includes clause 12, wherein the first magnet includes samarium-cobalt.

Clause 18: In some examples, the prosthesis includes any one of clauses 1-17, wherein the third magnetic portion is integral to the tibial component.

Clause 19: In some examples, the prosthesis includes any one of clauses 1-17, wherein the fourth magnetic portion is integral to the tibial component.

Clause 20: In some examples, the prosthesis includes clause 19, wherein the third magnetic portion is integral to the tibial component.

Clause 21: In some examples, the prosthesis includes any one of clauses 1-17, wherein the fourth magnetic portion includes a magnet.

Clause 22: In some examples, the prosthesis includes any one of clauses 1-17, wherein the third magnetic portion includes a first magnet.

Clause 23: In some examples, the prosthesis includes clause 22, wherein the fourth magnetic portion includes a second magnet.

Clause 24: In some examples, the prosthesis includes either one of clauses 22 or 23, wherein the third magnet includes a magnetic shim.

Clause 25: In some examples, the prosthesis includes either one of clauses 22 or 23, wherein the third magnet includes a rare earth magnet.

Clause 26: In some examples, the prosthesis includes clause 25, wherein the third magnet includes neodymium-iron-boron.

Clause 27: In some examples, the prosthesis includes clause 25, wherein the third magnet includes samarium-cobalt.

Clause 28: In some examples, the prosthesis includes any one of clauses 1-17, wherein the tibial bearing includes a bottom portion.

Clause 29: In some examples, the prosthesis includes clause 28, wherein the bottom portion of the tibial bearing is configured to be coupled to the top portion of the tibial component.

Clause 30: In some examples, the prosthesis includes either one of clauses 28 or 29, wherein the bottom portion of the tibial bearing includes one or more cavities configured for one or both of the third magnetic portion and/or fourth magnetic portion to be contained therein.

Clause 31: In some examples, the prosthesis includes any one of clauses 1-17, wherein the tibial component includes one or more cavities configured for one or both of the third magnetic portion and/or fourth magnetic portion to be contained therein.

Clause 32: In some examples, the prosthesis includes any one of clauses 1-17, wherein the tibial component includes a ferrous metal.

Clause 33: In some examples, the prosthesis includes clause 32, wherein the tibial component includes 400 series stainless steel.

Clause 34: In some examples, the prosthesis includes any one of clauses 1-17, wherein the tibial component includes nickel.

Clause 35: In some examples, the prosthesis includes any one of clauses 1-17, wherein the tibial component includes cobalt.

Clause 36: In some examples, the prosthesis includes clause 14, wherein the top portion of the femoral component includes a first face.

Clause 37: In some examples, the prosthesis includes clause 36, wherein the magnetic shim is configured to be coupled in a flush manner to the first face.

Clause 38: In some examples, the prosthesis includes clause 36, wherein the top portion of the femoral component includes a second face that is non-parallel to the first face.

Clause 39: In some examples, the prosthesis includes clause 38, wherein the magnetic shim is configured to be coupled in a flush manner to the second face.

Clause 40: In some examples, the prosthesis includes clause 38, wherein the top portion of the femoral component includes a third face that is non-parallel to the first face.

Clause 41: In some examples, the prosthesis includes clause 40, wherein the magnetic shim is configured to be coupled in a flush manner to the third face.

Clause 42: In some examples, the prosthesis includes any one of the preceding clauses, wherein the tibial component and the tibial bearing are configured to be snapped together.

Clause 43: In some examples, the prosthesis includes any one of the preceding clauses, wherein the tibial component and the tibial bearing are configured to be screwed together.

Clause 44: In some examples, the prosthesis includes any one of the preceding clauses, wherein the tibial bearing includes UHMWPE.

Clause 45: In some examples, the prosthesis includes any one of the preceding clauses, wherein the tibial bearing includes HXLPE.

Clause 46: In some examples, the prosthesis includes any one of the preceding clauses, wherein the tibial component includes an alloy including cobalt and chromium.

Clause 47: In some examples, the prosthesis includes any one of the preceding clauses, wherein the femoral component includes an alloy including cobalt and chromium.

Clause 48: In some examples, the prosthesis includes clause 1, wherein the first repulsive force is between about 0.1 pounds and about 30 pounds at a distance between the first pole and the fifth pole of about 0.25 inch.

Clause 49: In one example, an orthopedic knee prosthesis includes a femoral component having a top portion and a bottom portion, the femoral component including a femoral coupler configured to couple to a lower portion of a femur, the bottom portion including a curved medial condyle surface and a curved lateral condyle surface, a tibial bearing having a top portion including: a concave medial bearing surface configured to articulate with the curved medial condyle surface, and a concave lateral bearing surface configured to articulate with the curved lateral condyle surface, a tibial component having a bottom portion and a top portion, the bottom portion including a tibial coupler configured to couple to an upper portion of a tibia, the top portion including a tibial bearing coupler configured to couple to the tibial bearing, a first magnetic portion associated with the femoral component and configured to be in proximity to at least a portion of at least one of the curved medial condyle surface or the curved lateral condyle surface, the first magnetic portion having a first pole and a second pole, the second pole having the opposite polarity of the first pole, and a second magnetic portion associated with one or both of the tibial bearing and/or the tibial component and configured to be in proximity to at least a portion of at least one of the concave medial bearing surface or the concave lateral bearing surface, the second magnetic portion having a third pole and a fourth pole, the fourth pole having the opposite polarity of the third pole, wherein the third pole has the same polarity as the first pole, and wherein when (a) the tibial bearing is coupled to the tibial component and (b) the concave bearing surface articulates with the curved condyle surface: the third pole is configured to substantially oppose the first pole in sufficient proximity to thereby produce a first repulsive force.

Clause 50: In some examples, the prosthesis includes clause 49, wherein the first repulsive force is between about 0.1 pounds and about 60 pounds at a distance between the first pole and the third pole of about 0.25 inch.

Clause 51: In some examples, the prosthesis includes clause 50, wherein the first repulsive force is between about 0.2 pounds and about 60 pounds at a distance between the first pole and the third pole of about 0.25 inch.

Clause 52: In some examples, the prosthesis includes any one of clauses 49-51, wherein the first magnetic portion is integral to the femoral component.

Clause 53: In some examples, the prosthesis includes any one of clauses 49-52, wherein the second magnetic portion is integral to the tibial bearing.

Clause 54: In some examples, the prosthesis includes any one of clauses 49-52, wherein the second magnetic portion is integral to the tibial component.

Clause 55: In some examples, the prosthesis includes any one of clauses 49-54, wherein the second magnetic portion includes a magnet.

Clause 56: In some examples, the prosthesis includes any one of clauses 49-54, wherein the first magnetic portion includes a first magnet.

Clause 57: In some examples, the prosthesis includes clause 56, wherein the second magnetic portion includes a second magnet.

Clause 58: In some examples, the prosthesis includes either one of clauses 56 or 57, wherein the first magnet includes a magnetic shim.

Clause 59: In some examples, the prosthesis includes either one of clauses 56 or 57, wherein the first magnet includes a rare earth magnet.

Clause 60: In some examples, the prosthesis includes clause 59, wherein the first magnet includes neodymium-iron-boron.

Clause 61: In some examples, the prosthesis includes clause 59, wherein the first magnet includes samarium-cobalt.

Clause 62: In some examples, the prosthesis includes any one of clauses 49-61, wherein the tibial bearing includes a bottom portion.

Clause 63: In some examples, the prosthesis includes clause 62, wherein the bottom portion of the tibial bearing is configured to be coupled to the top portion of the tibial component.

Clause 64: In some examples, the prosthesis includes either one of clauses 62 or 63, wherein the bottom portion of the tibial bearing includes one or more cavities configured for the second magnetic portion to be contained therein.

Clause 65: In some examples, the prosthesis includes any one of clauses 49-64, wherein the tibial component includes a ferrous metal.

Clause 66: In some examples, the prosthesis includes clause 65, wherein the tibial component includes 400 series stainless steel.

Clause 67: In some examples, the prosthesis includes any one of clauses 49-66, wherein the tibial component includes nickel.

Clause 68: In some examples, the prosthesis includes any one of clauses 49-67, wherein the tibial component includes cobalt.

Clause 69: In some examples, the prosthesis includes clause 58, wherein the top portion of the femoral component includes a first face.

Clause 70: In some examples, the prosthesis includes clause 69, wherein the magnetic shim is configured to be coupled in a flush manner to the first face.

Clause 71: In some examples, the prosthesis includes clause 69, wherein the top portion of the femoral component includes a second face that is non-parallel to the first face.

Clause 72: In some examples, the prosthesis includes clause 71, wherein the magnetic shim is configured to be coupled in a flush manner to the second face.

Clause 73: In some examples, the prosthesis includes clause 71, wherein the top portion of the femoral component includes a third face that is non-parallel to the first face.

Clause 74: In some examples, the prosthesis includes clause 73, wherein the magnetic shim is configured to be coupled in a flush manner to the third face.

Clause 75: In some examples, the prosthesis includes any one of clauses 49-74, wherein the tibial component and the tibial bearing are configured to be snapped together.

Clause 76: In some examples, the prosthesis includes any one of clauses 49-75, wherein the tibial component and the tibial bearing are configured to be screwed together.

Clause 77: In some examples, the prosthesis includes any one of clauses 49-76, wherein the tibial bearing includes UHMWPE.

Clause 78: In some examples, the prosthesis includes any one of clauses 49-77, wherein the tibial bearing includes HXLPE.

Clause 79: In some examples, the prosthesis includes any one of clauses 49-78, wherein the tibial component includes an alloy including cobalt and chromium.

Clause 80: In some examples, the prosthesis includes any one of clauses 49-79, wherein the femoral component includes an alloy including cobalt and chromium.

Clause 81: In some examples, the prosthesis includes any one of clauses 1-48, and further includes a magnetic shield adjacent at least one of the first magnetic portion, the second magnetic portion, the third magnetic portion, and/or the fourth magnetic portion.

Clause 82: In some examples, the prosthesis includes clause 81, wherein the magnetic shield includes one or more material selected from the list consisting of: nickel, iron, molybdenum, and silicon.

Clause 83: In some examples, the prosthesis includes any one of clauses 49-80, and further includes a magnetic shield adjacent at least one of the first magnetic portion, and/or the second magnetic portion.

Clause 84: In some examples, the prosthesis includes clause 83, wherein the magnetic shield includes one or more material selected from the list consisting of: nickel, iron, molybdenum, and silicon.

Clause 85: In one example a method of performing a total knee arthroplasty includes providing the prosthesis of any one of clauses 1-80, and implanting the prosthesis within a patient.

While the foregoing is directed to embodiments of the present disclosure, other and further embodiments may be devised without departing from the basic scope thereof. Alternatively, embodiments may comprise the implant of a magnet similar to the magnet 178, such that it is implanted directly into a cavity cut into the tibia. The magnet can be cemented directly into the cavity cut in the tibia, and covered by the cement, in order to protect the magnet both chemically and against stresses. In some embodiments, polymethyl methacrylate (PMMA) cement can be utilized.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

For purposes of the present disclosure and appended claims, the conjunction "or" is to be construed inclusively (e.g., "an apple or an orange" would be interpreted as "an apple, or an orange, or both"; e.g., "an apple, an orange, or an avocado" would be interpreted as "an apple, or an orange, or an avocado, or any two, or all three"), unless: (i) it is explicitly stated otherwise, e.g., by use of "either . . . or," "only one of," or similar language; or (ii) two or more of the listed alternatives are mutually exclusive within the particular context, in which case "or" would encompass only those combinations involving non-mutually-exclusive alternatives. For purposes of the present disclosure and appended claims, the words "comprising," "including," "having," and variants thereof, wherever they appear, shall be construed as open-ended terminology, with the same meaning as if the phrase "at least" were appended after each instance thereof.

What is claimed is:

1. An orthopedic knee prosthesis comprising:
   a femoral component comprising a top portion comprising a femoral coupler configured to couple to a lower portion of a femur, and a bottom portion comprising a curved medial condyle surface and a curved lateral condyle surface;
   a tibial bearing comprising a top portion comprising a concave medial bearing surface configured to articulate with the curved medial condyle surface and a concave lateral bearing surface configured to articulate with the curved lateral condyle surface;
   a tibial component comprising a bearing coupler configured to couple to the tibial bearing and a bottom portion comprising a tibial coupler configured to couple to an upper portion of a tibia;
   a first magnetic portion associated with the femoral component and comprising a first pole having a first pole polarity, the first magnetic portion not physically interrupting any articulating portion of the curved medial condyle surface and not physically interrupting any articulating portion of the curved lateral condyle surface; and
   a second magnetic portion associated with one or both of the tibial bearing and/or the tibial component and comprising a second pole having a second pole polarity, the second pole polarity the same as the first pole polarity, the second magnetic portion not physically interrupting any articulating portion of the concave medial bearing surface and not physically interrupting any articulating portion of the concave lateral bearing surface, wherein, when the curved medial condyle surface is articulatably coupled to the concave medial bearing surface and the curved lateral condyle surface is articulatably coupled to the concave lateral bearing surface, the first pole and the second pole are in sufficient proximity to each other such that a magnetic repulsive force is present, the repulsive force configured to subtract from compressive forces that are applied between the femoral component and the tibial bearing, wherein the curved medial condyle surface and the curved lateral condyle surface together define a first side of a condyle structure, and wherein a second side of the condyle structure, opposite the first side, comprises one or more cavity configured for the first magnetic portion to be contained therein, the one or more cavity not extending through the first side.

2. The prosthesis of claim 1, wherein the one or more cavity comprises a first medial cavity and a first lateral cavity, the first medial cavity and the first lateral cavity configured to be opposite the femoral coupler.

3. The prosthesis of claim 2, wherein the one or more cavity further comprises a second medial cavity and a second lateral cavity, the second medial cavity adjacent to and angled from the first medial cavity and the second lateral cavity adjacent to and angled from the first lateral cavity.

4. The prosthesis of claim 3, wherein the wherein the second medial cavity is angled from the first medial cavity by an obtuse angle.

5. The prosthesis of claim 2, wherein the first medial cavity and the first lateral cavity are configured to snappably receive a first permanent magnet and a second permanent magnet which comprise the first magnetic portion.

6. The prosthesis of claim 2, further comprising a first permanent magnet bonded within the first medial cavity and a second permanent magnet bonded within the first lateral cavity.

7. An orthopedic knee prosthesis comprising:
   a femoral component comprising a top portion comprising a femoral coupler configured to couple to a lower portion of a femur, and a bottom portion comprising a curved medial condyle surface and a curved lateral condyle surface;
   a tibial bearing comprising a top portion comprising a concave medial bearing surface configured to articulate with the curved medial condyle surface and a concave lateral bearing surface configured to articulate with the curved lateral condyle surface;
   a tibial component comprising a bearing coupler configured to couple to the tibial bearing and a bottom portion comprising a tibial coupler configured to couple to an upper portion of a tibia;
   a first magnetic portion associated with the femoral component and comprising a first pole having a first pole polarity, the first magnetic portion not physically interrupting any articulating portion of the curved medial condyle surface and not physically interrupting any articulating portion of the curved lateral condyle surface; and a second magnetic portion associated with one or both of the tibial bearing and/or the tibial component and comprising a second pole having a second pole polarity, the second pole polarity the same as the first pole polarity, the second magnetic portion not physically interrupting any articulating portion of the concave medial bearing surface and not physically interrupting any articulating portion of the concave lateral bearing surface, wherein, when the curved medial condyle surface is articulatably coupled to the concave medial bearing surface and the curved lateral condyle surface is articulatably coupled to the concave lateral bearing surface, the first pole and the second pole are in sufficient proximity to each other such that a magnetic repulsive force is present, the repulsive force configured to subtract from compressive forces that are applied between the femoral component and the tibial bearing, wherein the bearing coupler of the tibial component comprises a tibial component cavity that extends from a top portion of the tibial component into the bottom portion of the tibial component, wherein the tibial coupler comprises a stem, and wherein the tibial component cavity extends within the stem, and wherein the second magnetic portion is configured to extend to a portion of the tibial component cavity within the stem.

* * * * *

UNITED STATES PATENT AND TRADEMARK OFFICE
CERTIFICATE OF CORRECTION

| | |
|---|---|
| PATENT NO. | : 11,969,351 B2 |
| APPLICATION NO. | : 18/260465 |
| DATED | : April 30, 2024 |
| INVENTOR(S) | : James M. Jackson |

It is certified that error appears in the above-identified patent and that said Letters Patent is hereby corrected as shown below:

In the Claims

Column 30, Claim 4, Line 1: delete the second "wherein the"

Signed and Sealed this
Third Day of September, 2024

Katherine Kelly Vidal
*Director of the United States Patent and Trademark Office*